(12) United States Patent
Freudenthal et al.

(10) Patent No.: US 9,683,930 B2
(45) Date of Patent: Jun. 20, 2017

(54) POLARIZATION PROPERTIES IMAGING SYSTEMS

(71) Applicant: Hinds Instruments, Inc., Hillsboro, OR (US)

(72) Inventors: John Freudenthal, Hillsboro, OR (US); Andy Leadbetter, Hillsboro, OR (US); Baoliang Wang, Portland, OR (US)

(73) Assignee: Hinds Instruments, Inc., Hillsboro, OR (US)

(*) Notice: Subject to any disclaimer, the term of this patent is extended or adjusted under 35 U.S.C. 154(b) by 0 days.

(21) Appl. No.: 14/893,157

(22) PCT Filed: May 20, 2014

(86) PCT No.: PCT/US2014/038837
§ 371 (c)(1),
(2) Date: Nov. 23, 2015

(87) PCT Pub. No.: WO2014/189967
PCT Pub. Date: Nov. 27, 2014

(65) Prior Publication Data
US 2016/0116397 A1 Apr. 28, 2016

Related U.S. Application Data

(60) Provisional application No. 61/826,663, filed on May 23, 2013, provisional application No. 61/927,354, filed on Jan. 14, 2014.

(51) Int. Cl.
*G01J 4/00* (2006.01)
*G01N 21/23* (2006.01)
*G01N 21/21* (2006.01)

(52) U.S. Cl.
CPC ............. *G01N 21/23* (2013.01); *G01J 4/00* (2013.01); *G01N 21/21* (2013.01); *G01N 2201/0621* (2013.01); *G01N 2201/0683* (2013.01)

(58) Field of Classification Search
CPC ............ G01N 21/21; G01N 21/23; G01N 2201/0621; G01N 2201/0683; G01J 4/00
(Continued)

(56) References Cited

U.S. PATENT DOCUMENTS

| 4,708,473 A | 11/1987 | Metzdorff et al. |
| 4,865,450 A * | 9/1989 | Munechika ............... G01J 9/04 356/489 |

(Continued)

FOREIGN PATENT DOCUMENTS

| FR | 2529338 | 12/1983 |
| JP | 2009-109439 | 5/2009 |

(Continued)

OTHER PUBLICATIONS

International Search Report and Written Opinion for related International Application No. PCT/US2014/038837, mailed Nov. 20, 2014, 13 pages.

(Continued)

*Primary Examiner* — Hina F Ayub
(74) *Attorney, Agent, or Firm* — Klarquist Sparkman, LLP

(57) ABSTRACT

This disclosure is generally directed to systems for imaging polarization properties of optical-material samples. As one example, there is provided a system for precise, simultaneous imaging of both the in-plane and out-of-plane birefringence properties of sample material over a wide range of incidence angles. An example spatially resolved imaging approach described herein is amenable to determination of a (Continued)

wide range of polarimetric properties, in addition to the in-plane and out-of-plane birefringence measure discussed as a preferred embodiment.

11 Claims, 13 Drawing Sheets

(58) Field of Classification Search
USPC .......................................................... 356/370
See application file for complete search history.

(56) References Cited

U.S. PATENT DOCUMENTS

| | | | |
|---|---|---|---|
| 5,286,968 | A | 2/1994 | Fournier et al. |
| 6,134,012 | A | 10/2000 | Aspnes et al. |
| 6,157,448 | A | 12/2000 | Kowa et al. |
| 6,348,966 | B1 | 2/2002 | Hirosawa |
| 6,697,157 | B2 | 2/2004 | Wang et al. |
| 7,064,828 | B1 * | 6/2006 | Rovira .................... G01J 3/447 356/369 |
| 7,312,869 | B2 | 12/2007 | Wang |
| 7,369,234 | B2 | 5/2008 | Beaglehole |
| 7,586,607 | B2 | 9/2009 | Sun |
| 2001/0007496 | A1 | 7/2001 | Modlin |
| 2004/0042009 | A1 | 3/2004 | Aspnes et al. |
| 2005/0134849 | A1 | 6/2005 | Beaglehole |
| 2011/0063617 | A1 | 3/2011 | Takahashi |
| 2014/0003823 | A1 * | 1/2014 | Roberts ................ H04B 10/116 398/187 |

FOREIGN PATENT DOCUMENTS

| | | |
|---|---|---|
| WO | WO 2004/070365 | 8/2004 |
| WO | WO 2013/104744 | 7/2013 |
| WO | WO 2013/138090 | 9/2013 |
| WO | WO 2014/189967 | 11/2014 |

OTHER PUBLICATIONS

Andert, et al., "An Instrument for Measuring Circular Dichroism Simultaneously at all Wavelengths in a Limited Spectral Range," *Review of Scientific Instruments*, 62(8):1912-1915 (Aug. 1, 1991).

Collins et al., "Dual rotating-compensator multichannel ellipsometer: instrument design for real-time Mueller matrix spectroscopy of surfaces and films," *Journal of the Optical Society of America*, 16(8):1997-2006 (Aug. 8, 1999).

Dubois et al., "High-resolution full-field optical coherence tomography with a Linnik microscope," *Applied Optics*, 41(4):805-812 (Feb. 1, 2002).

European Search Report for related Application No. 07706394.6, 8 pages, mailed May 19, 2008.

Extended European Search Report for related Application No. 13760626.5, 5 pages, mailed Oct. 19, 2015.

Gleyzes et al., "Multichannel Nomarski Microscope with Polarization Modulation: Performance and Applications," *Optics Letters* 22(20):1529-1531 (Oct. 15, 1997).

Sun et al., "High Throughput Polarization Imaging for Defocus and Dose Inspection for Production Wafers," Rudolph technologies, 4 pages (Feb. 2007).

* cited by examiner

POLARIZATION PROPERTIES IMAGING SYSTEMS

CROSS REFERENCE TO RELATED APPLICATIONS

This is the U.S. National Stage of International Application No. PCT/US2014/038837, filed May 20, 2014, which was published in English under PCT Article 21(2), which in turn claims the benefit of U.S. Provisional Application No. 61/927,354, filed Jan. 14, 2014 and U.S. Provisional Application No. 61/826,663, filed May 23, 2013, all of which are hereby incorporated herein in their entirety.

TECHNICAL FIELD

This application relates to systems for imaging polarization properties of optical-material samples. One example of such a system provides simultaneous imaging of both the in-plane and out-of-plane birefringence properties of a sample over a wide range of incidence angles.

BACKGROUND

Many important optical materials exhibit birefringence. Birefringence causes different linear polarizations of light to travel at different speeds through the material. These different polarizations are most often considered as two components of the polarized light, one component being orthogonal to the other.

Birefringence is an intrinsic property of many optical materials, and may also be induced by external forces applied to the material. The induced birefringence may be temporary, as when the material is oscillated, or the birefringence may be residual, as when the material undergoes thermal stress during production.

Retardation or retardance represents the integrated effect of birefringence acting along the path of a light beam that traverses a sample of the optical material. If the incident light beam is linearly polarized, the two orthogonal components of the polarized light will exit the sample with a phase difference, called the retardance. The fundamental unit of retardance is length, such as nanometers (nm). A second convenient expression of retardance is units of phase angle (waves, radians, or degrees), which is the retardance (nm) divided by the wavelength of the light (nm). A "normalized" birefringence for a sample is sometimes computed by dividing the measured retardance magnitude by the thickness of the sample.

The two orthogonal, polarized beam components mentioned above are parallel to two orthogonal axes associated with the optical material, which axes are referred to as the "fast axis" and the "slow axis." The fast axis is the axis of the material that aligns with the faster moving component of the polarized light through the sample. A complete description of the retardance of a sample along a given optical path requires specifying both the magnitude of the retardance and the relative angular orientation of the fast (or slow) axis of the sample.

The need for precise measurement of birefringence properties has become increasingly important in a number of technical applications, such as the metrology of linear birefringence in optical elements that are used in high-precision instruments employed in semiconductor and other industries.

The prior art, including U.S. Pat. No. 6,473,179, Birefringence Measurement System, hereby incorporated by reference, discloses methods and apparatus for measuring birefringence of a sample using a light beam that is directed through the sample at a normal (zero-degree) incidence angle relative to the surface of the sample. As a result, the determination of the sample's birefringence is "in-plane" or "normal," meaning that the determination essentially represents the difference between the indices of refraction of two orthogonal axes in a plane of the sample, that plane being normal to the incident light beam. The term "in-plane retardance" or "normal retardance" means the product of the in-plane birefringence and the thickness of the optical sample being measured.

Prior systems, such as that disclosed in the above-noted U.S. Pat. No. 6,473,179, can be designated "point based measurement systems" because the birefringence data is collected for a single point or location in the sample, one point at a time. Such systems are particularly useful with samples having extremely low to mid-range levels of birefringence.

Many display techniques rely on the control of polarized light, and the birefringence of the materials used in systems, such as liquid crystal display (LCD) panels, affect the resulting color and contrast of the image. For liquid crystals and many materials, the extent or magnitude of birefringence is a function of the incident angle of the light under consideration. For example, increasing (from normal) the viewing angle of an LCD panel will increase the birefringence effect on the light emanating from the panel and, without compensation, that increase reduces the perceived quality of the visible light by reducing contrast and/or altering colors. When viewed in normal incidence, the speed of light is affected by two orthogonal refractive indices, $n_x$ and $n_y$. The birefringence is a function of the difference in these two properties. When in non-normal incidence, the light is also affected by the third orthogonal refractive index, $n_z$.

Transparent polymer films have been developed for use with LCD panels for the purpose of compensating for the just-noted birefringence variations attributable to viewing angle. In short, these films possess birefringence characteristics that compensate for the birefringence of the LCD panel and thus provide a wide viewing angle without significant loss of contrast or color.

Characterizing the effective birefringence of such films, and other optical materials, in planes that are not normal (zero-degree) to the angle of incidence allows for the optimization, control and analysis of such materials. This birefringence measure can be referred to as "out-of-plane" birefringence. One can consider the notion of in-plane and out-of-plane birefringence in terms of a Cartesian coordinate system. Accordingly, if the normal-incidence light is considered to travel in a direction parallel to the Z-axis of such a coordinate system, the in-plane birefringence occurs in the XY plane of the sample. Out-of-plane birefringence is in a plane not coincident to the in-plane (XY plane) birefringence. Special cases occur in the XZ or YZ plane, which planes are perpendicular to the XY plane. The terms vertical birefringence and "$R_{th}$", are specifically used for those special cases. $R_{th}$ means the product of the vertical (XZ or YZ) birefringence and the thickness of the optical sample being measured.

Other applications, in addition to the birefringence compensation film example just discussed, may also call for precise determination of out-of-plane birefringence. For example, uniaxial crystals have a unique optical axis (Z-axis). A light beam that propagates perpendicular to this axis experiences the maximal intrinsic birefringence. A light beam that propagates along this axis experiences no intrinsic birefringence. The birefringence on either XZ or YZ plane is the "out-of-plane" birefringence for a light beam propagating along the Z-axis. .

In U.S. Pat. No. 7,312,869 ("'869 Patent"), hereby incorporated by reference, there is disclosed a point based method and apparatus for precise measurement of out-of-plane birefringence properties of samples of transparent optical material. Two angled-apart, polarization-modulated light beams are passed through a selected location of the sample optical element. One of the beams is normal or zero-degree incident to the sample surface, and the other beam is oblique to that surface. The characteristics of the beams are detected after passing through the sample, and the information detected is processed to determine the out-of-plane birefringence.

As described in the '869 Patent, the out-of-plane birefringence calculation involves information derived from both the normally incident and oblique beams. Accordingly, in the two-beam approach described there, the single sample location through which the oblique-angled beam penetrates is substantially aligned with, and not significantly different in size than, the location through which the normal-incidence beam penetrates.

As noted above, with many materials the extent or magnitude of birefringence is a function of the incident angle of the light under consideration, and increasing (from normal) the viewing angle of a LCD panel will increase the birefringence effect on the light emanating from the panel. To measure the birefringence of such material at several different angles (thereby to design a suitable compensation film, for example), several measurements must be made over a range of oblique-angle incidences. In a point based system such as that described in the '869 Patent, the sample may be sequentially tilted into several discrete angular positions and at each position the oblique-angled beam is directed through the sample to detect the associated birefringence information for that particular angle. To yield improved results, measurements at multiple angles of incidence can be taken. These multiple measurements are usually done sequentially by mechanically rotating or tilting the sample. These numerous sequential measurements require significant amounts of time to complete.

Irrespective of the particular polarization properties of interest, such as in-plane birefringence only, or both in-plane and out-of-plane birefringence, certain optical-material samples may have configurations and birefringence characteristics that make them amenable to imaging techniques for rapidly collecting across a wide area of the sample the data employed for calculating the sought-after properties. An imaging system for collecting such data across an area of (or the entire area of) a sample will provide high spatial resolution and is particularly useful for low to high levels of birefringence, that is, where the sample is not characterized by extremely low levels of birefringence.

SUMMARY OF THE INVENTION

The present invention is generally directed to systems for imaging polarization properties of optical-material samples. As one aspect of this invention, there is provided a system for precise, simultaneous imaging of both the in-plane and out-of-plane birefringence properties of sample material over a wide range of incidence angles. The spatially resolved imaging approach described here is amenable to determination of a wide range of polarimetric properties, in addition to the in-plane and out-of-plane birefringence measure discussed as a preferred embodiment.

The preferred embodiments of imaging systems of the present invention include an optical train having two or more oscillating photoelastic modulators (PEMs) for highly stable modulation of the polarization of the light that is directed through the sample. The imaging detector for the spatially resolved (and polarization modulated) beam comprises a CMOS or CCD-type camera. The operational frequency of such devices, which are integrating detectors, can be relatively slow, and generally an order of magnitude slower than the oscillation of the PEMs. This long integration or exposure time would, in the absence of the present invention, have the undesired effect of averaging out the oscillating signal produced by the PEMs.

Put another way, the problem is that a relatively slow camera/detector cannot be driven at the high modulation frequency of the PEM. The present invention provides ways to address this problem by gating the light source or the imaging detector in a manner such that the detector only receives light pulses in instances when the PEMs are in a known state so that the collected image (intensity) data is useful for accurately calculating the birefringence properties, as described below.

In some instances, however, such gating or pulsing of the light source, may result in a poor exposure-time-to-intensity ratio that, for some samples, may produce substantial and undesirable dark current and light pollution noise. Another aspect of this invention provides a system that addresses this problem by employing a gating mechanism that is operated by a trigger signal that is based on the frequency synthesis of the combined output signals from the PEMs. Among other things, the trigger signal generated in accord with the present invention permits gating that ensures that at least 50% of the available light intensity is received by the imaging device.

Other advantages and features of the present invention will become clear upon study of the following portion of this specification and the drawings.

DETAILED DESCRIPTION

Figure 1:
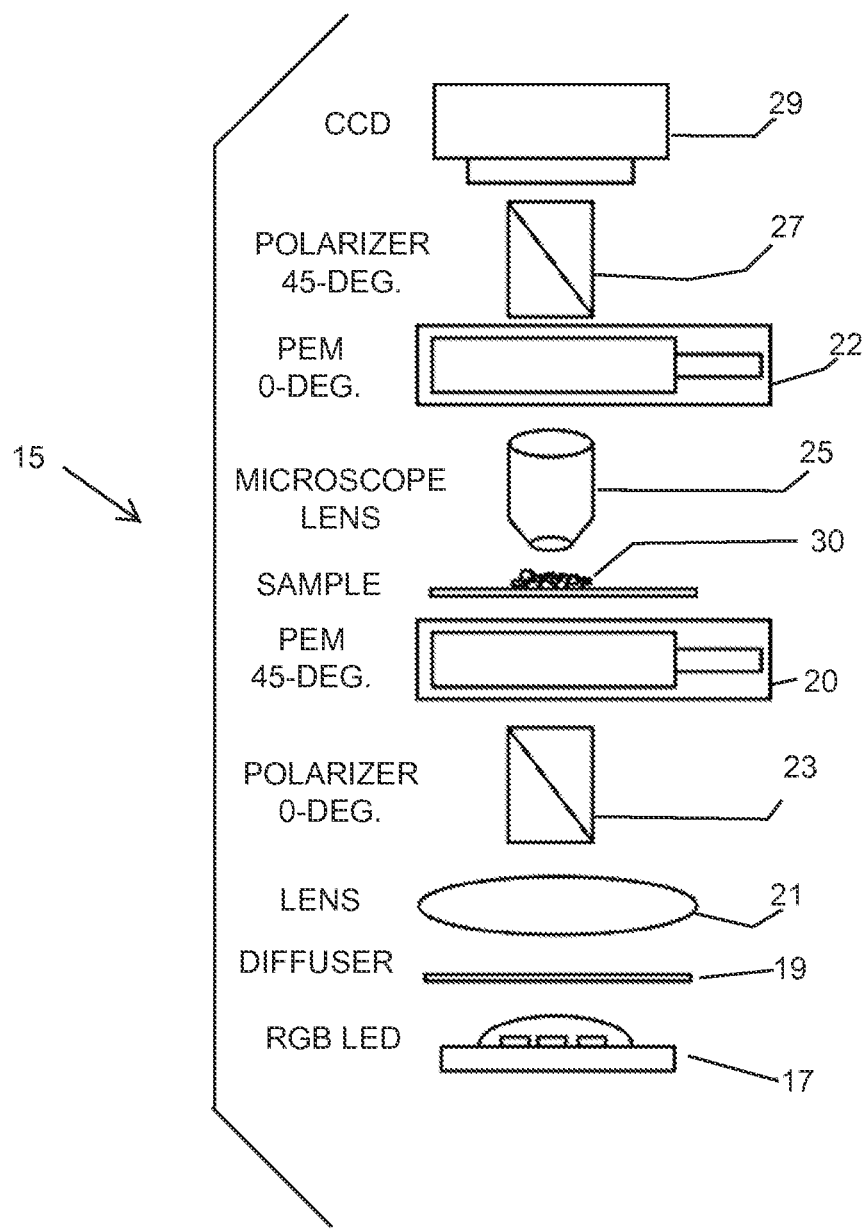
FIG. 1 is a diagram showing one preferred arrangement of the optical components of a system that may be used for imaging polarization properties, such as birefringence, across an area of a sample.

FIG. 1 depicts one preferred arrangement or "setup" of optical components of a system 15 that may be used for imaging polarization properties, such as birefringence, across an area of a sample. That system includes a light source 17 that directs light (upwardly in the setup of FIG. 1) through a sample 30 to an imaging device 29 such as a conventional CMOS or CCD-type camera. The light source is, preferably, a LED having individually controlled diodes emitting red ("R," having, for example, a wavelength of 630 nanometers, nm), green ("G," having, for example, a wavelength of 530, nm) and blue ("B," having, for example, a wavelength of 470 nm) that are, preferably, sequentially turned ON and OFF, or "triggered." (For measurements requiring lower precision, the system can employ an RGB Bayer filter camera and record red, green, and blue retardance values simultaneously.)

The light from the source 17 passes through a diffuser 19 and lens 21 from which propagates a relatively wide, collimated beam that passes through a polarizer 23 oriented at 0° relative to the baseline axis of the setup.

The polarized light emanating from the polarizer 23 is incident upon the optical element of a first photoelastic modulator ("PEM") 20. In a preferred embodiment, the PEM is one manufactured by Hinds Instruments, Inc., of Hillsboro, Oregon. The use of PEMs for modulating the polarization of the source light is preferred because of its fast modulation, insensitivity to angle of propagation, large aperture, high precision, and large spectral range. It is contemplated, however, that other mechanisms could be used for modulating the polarization of the source light, such as electro-optic modulators, liquid crystal retarders, and mechanically modulated waveplates.

The PEM 20 has its birefringent axis oriented at 45° and is controlled by an associated controller that imparts an oscillating birefringence to the optical element of the PEM, preferably at a nominal frequency of 42 kHz. In this regard, the controller drives one or more quartz transducers that are adhered to the optical element of the PEM 20.

The oscillating birefringence of the PEM 20 introduces a time-varying phase difference between the orthogonal components of the polarized light that propagates through the PEM. At any instant in time, the phase difference represents the retardation introduced by the PEM. As noted earlier, the retardation is measurable in units of length, such as nanometers. The PEM 20 is adjustable to allow variation of the amplitude of the retardation introduced by the PEM.

With continued reference to FIG. 1, the light emanating from the sample 30 is directed through a lens 25—in this embodiment a microscope lens—to a second PEM 22 that is controlled by an associated controller to operate at a modulation frequency (for example, 47 kHz) that is different from the modulation frequency of the first PEM 20. The second PEM 22 is oriented at 0°. A second polarizer 27, oriented at 45°, is between the second PEM 22 and the CCD 29.

It is noteworthy here that the system configuration illustrated in FIG. 1 includes microscope lensing and, as such, is useful for imaging small or microscopic fields of, for example 200 μm² to 1 cm² in area, with 2× to 10× magnification and 1-8 megapixel (MP) resolution. It will be appreciated that the imaging lensing components of the systems described herein can be varied as needed to accommodate much larger fields for imaging corresponding large samples. Both Köhler and telecentric (including a diffuser) sample illumination methods may be employed, among others.

With continued reference to FIG. 1, the CCD 29 includes individual pixels, each of which receives light passing through a particular point of the sample 30 so that the light intensity captured in each pixel corresponds to the birefringence characteristics of that particular point. In particular, for each point in the sample the quantity of interest is retardance, $\delta$, and angle of the fast axis, $\theta$. Expressed as a 4×4 Mueller matrix below.

$$M_{bir}(\delta_S, \delta_S) = \begin{bmatrix} 1 & 0 & 0 & 0 \\ 0 & M_{11} & M_{12} & -\sin(2\theta_S)\sin(\delta_S) \\ 0 & -M_{12} & M_{22} & \cos(2\theta_S)\sin(\delta_S) \\ 0 & \sin(2\theta_S)\sin(\delta_S) & -\cos(2\theta_S)\sin(\delta_S) & \cos(\delta_S) \end{bmatrix}$$

In summary, the optical path for the dual-PEM birefringence imaging microscope system of FIG. 1 comprises an LED light source, a linear polarizer, a PEM, the sample, a second PEM, a second linear polarizer, and a CCD camera. For each pixel of the CCD, the sample's linear retardance, $\delta_S$, and angle of the fast axis, $\theta_S$, is measured.

The mathematics for the optical train are best expressed with Mueller matrices. The Mueller matrix for a linear polarizer is shown below.

$$M_{pol}(\theta) = \begin{bmatrix} 1 & C_\theta & S_\theta & 0 \\ C_\theta & C_\theta^2 & C_\theta S_\theta & 0 \\ S_\theta & C_\theta S_\theta & S_\theta^2 & 0 \\ 0 & 0 & 0 & 0 \end{bmatrix}$$

In the equation above, $C_\theta = \cos\theta$, and $S_\theta = \sin\theta$ where $\theta$ is the half angle of rotation of the linear polarizer.

The Mueller matrix for the PEMs is given below.

$$M_{PEM}(\theta, \delta) = \begin{bmatrix} 1 & 0 & 0 & 0 \\ 0 & C_\delta S_\theta^2 + C_\theta^2 & C_\theta S_\theta(1-C_\delta) & -S_\delta S_\theta \\ 0 & C_\theta S_\theta(1-C_\delta) & C_\delta C_\theta^2 + S_\theta^2 & \delta_\delta C_\theta \\ 0 & \delta_\delta S_\theta & -S_\delta C_\theta & C_\delta \end{bmatrix}$$

where $C_\delta = \cos\delta$, and $S_\delta = \sin\delta$ where $\delta(t) = A\cos(\omega t + \phi)$, A is the modulation amplitude, $\omega$ is the angular velocity of the photoelastic modulator, t is time, and $\phi$ is the phase delay of the photoelastic modulator.

The sample of interest is assumed to have a Mueller matrix that takes the form of a linear birefringent material, such as the PEM above, but here, the Mueller matrix of the sample is expressed using a generic lower-right-hand Mueller matrix as shown below.

$$M_S = \begin{bmatrix} M_{00} & 0 & 0 & 0 \\ 0 & M_{11} & M_{12} & M_{13} \\ 0 & M_{12} & M_{22} & M_{23} \\ 0 & -M_{13} & -M_{23} & M_{33} \end{bmatrix}$$

The elements of the sample Mueller matrix $M_{mn}$ are identical to $M_{PEM}(\theta, \delta)$ with $\delta=\theta_S$ and $\delta=\delta_S$ where $\theta_S$ is the angle of the fast axis, and $\delta_S$ is the retardance of the sample. These two quantities will be isolated later, but first the entire optical pathway is expressed in Mueller matrices for isolating the terms of interest.

$$M_{OT} = M_{pol}(0) M_{PEM}\left(\frac{\pi}{4}, \delta_2\right) M_S M_{PEM}(0, \delta_1) M_{pol}\left(\frac{\pi}{4}\right)$$

The time dependent intensity at the CCD is given by the 00 element of the Mueller matrix for the entire optical train, $M_{OT}$, and is shown below.

$$I(\delta_1, \delta_2) = M_{00} + C_{\delta 1} C_{\delta 2} M_{12} + C_{\delta 1} S_{\delta 2} M_{23} + S_{\delta 1} C_{\delta 2} M_{13} + S_{\delta 1} S_{\delta 2} M_{33}$$

The intensity expression is then vectorized to isolate the terms of interest, which are the elements of $M_S$.

$$I(\delta_1, \delta_2) = [1\ C_{\delta 1} C_{\delta 2}\ C_{\delta 1} S_{\delta 2}\ S_{\delta 1} C_{\delta 2}\ S_{\delta 1} S_{\delta 2}] [M_{00} M_{12} M_{23} M_{13} M_{33}]^T$$

In the above expression, T is the transpose operation. The light source is controlled to pulse only when both $\delta_1$ and $\delta_2$ are at a known value, as will be explained below. A number of images can be taken, and the vectors for each can be assembled into a complete matrix as shown below.

$$I = AM$$

$$I = \begin{bmatrix} I(\delta_{1A}, \delta_{2A}) \\ I(\delta_{1B}, \delta_{2B}) \\ \vdots \\ I(\delta_{1N}, \delta_{2N}) \end{bmatrix}$$

$$A = \begin{bmatrix} 1 & C_{\delta 1A} C_{\delta 2A} & C_{\delta 1A} C_{\delta 2A} & C_{\delta 1A} C_{\delta 2A} & C_{\delta 1A} C_{\delta 2A} \\ 1 & C_{\delta 1B} C_{\delta 2B} & C_{\delta 1B} C_{\delta 2B} & C_{\delta 1B} C_{\delta 2B} & C_{\delta 1B} C_{\delta 2B} \\ \vdots & \vdots & \vdots & \vdots & \vdots \\ 1 & C_{\delta 1N} C_{\delta 2N} & C_{\delta 1N} C_{\delta 2N} & C_{\delta 1N} C_{\delta 2N} & C_{\delta 1N} C_{\delta 2N} \end{bmatrix}$$

$$M = [M_{00}\ M_{12}\ M_{23}\ M_{13}\ M_{33}]^T$$

In the equation above, I is a vector of intensity values at different PEM retardance values, $\delta_1$ and $\delta_2$. The analyzer matrix, A, is comprised of the cosine and sine values at the known retardance values. The analyzer matrix's condition number is then optimized given the fewest feasible images. The equation is then inverted to solve for the quantities of M.

$$M = A^{-1} I$$

If more than 5 images are collected, a pseudo-inverse is used. From here, the linear retardance, $\delta_S$, and angle of the fast axis, $\theta_S$, are solved using the following equations.

$$\theta_S = \frac{1}{2} \tan 2^{-1}(M_{13}, M_{23})$$

$$\delta_S = \tan^{-1}\left(\sqrt{\left(\frac{M_{13}}{M_{33}}\right)^2 + \left(\frac{M_{23}}{M_{33}}\right)^2}\right)$$

Above, tan $2^{-1}$ is the four quadrant arc tangent.

The challenge is to detect the intensity only at given values of the PEMs. To accomplish this, the LED light source can be triggered for a short period during each cycle of the PEM as shown in FIG. 2 and discussed next.

Figure 2:
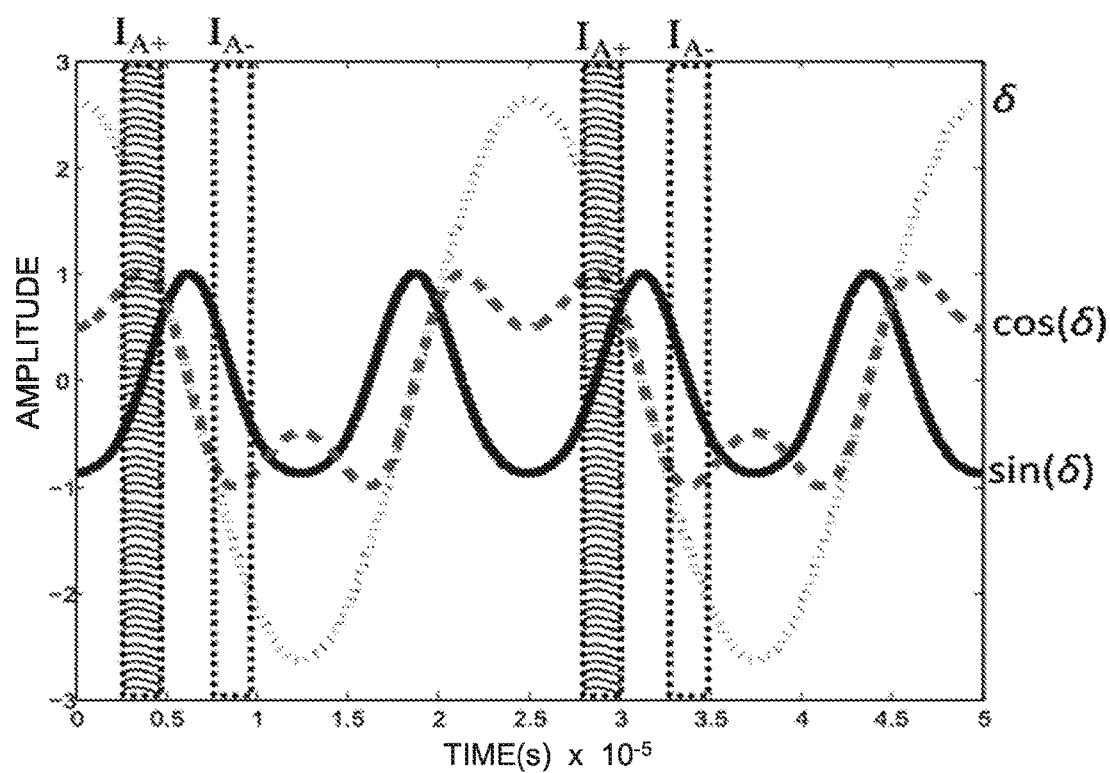
FIGS. 2 and 3 are diagrams illustrating one preferred method of triggering a light source at particular instances in relation to the operation of the PEM components of the optical setup.

FIG. 2 shows that as the retardance of the modulator changes, the sine and cosine of the retardance alternates between −1 and 1. Therefore, to measure the amplitude of the cosine component, cos(δ), two images can be collected by flashing the source light LED 17 at the times indicated by the dotted regions, $I_{A-}$, and dotted, waved regions, $I_{A+}$. The difference in intensity for these two images, $I_A$, is proportional to the component coupled with cos(δ).

$$I_A = \frac{I_{A+} - I_{A-}}{2}$$

In the optical train shown in FIG. 1, all the components of interest have two modulator birefringence terms. To collect these quantities, one of two methods can be used. The first method is identical to the graph and example above: collect the intensity whenever one of the two modulators is at a given phase. This will result in the cosine term of the other modulator being time-averaged as shown below in the Jacobi Anger expansion.

$$J_0[|A|] = \int_0^T \frac{\cos[\cos[t]]}{T} dt \approx \sum_{t=0}^T \frac{\cos[\cos[t]]}{T}$$

$$0 = \int_0^T \frac{\sin[\cos[t]]}{T} dt \approx \sum_{t=0}^T \frac{\sin[\cos[t]]}{T}$$

For example, the term $C_{\delta 1} C_{\delta 2}$ would become $\cos(\delta_1) J_0 [|A_2|]$ if the triggering was set to blink or pulse the LED in phase with the first modulator, and ignore the second. The problem with this scheme is that all the sine terms go to zero, and cannot be measured.

Figure 3:
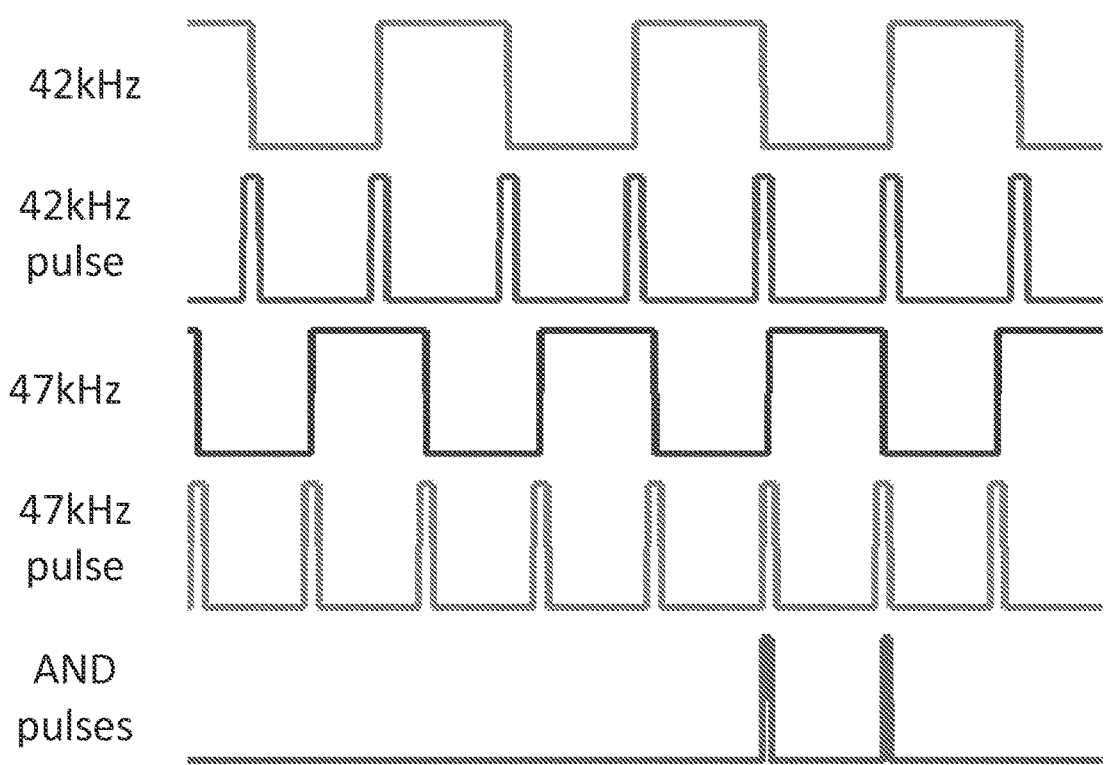

To measure a sine term, the triggering must take into account the operation of both modulators. This can be accomplished by a dedicated piece of hardware that watches both square waves generated by the PEMs and creates in-phase triggering pulses as above, while accounting for multiple modulators, and runs the resulting triggers through a logical AND gate to find a common result. This is illustrated in FIG. 3.

The problem with this approach (FIG. 3) is that while each modulator trigger is active for about 1% of the modulator cycle, the two triggers only fire in unison about 0.01% (1% of 1%) of the time. This infrequent occurrence of unison firing to generate a triggering signal or pulse means that exposure times for the detector/camera must be very large.

One way to address this above mentioned problem requiring long exposure times in instances where two or more PEMs are included in the optical setup is to use (have turned on) only one PEM at a time, which will be discussed next with reference to FIG. 4.

Figure 4:
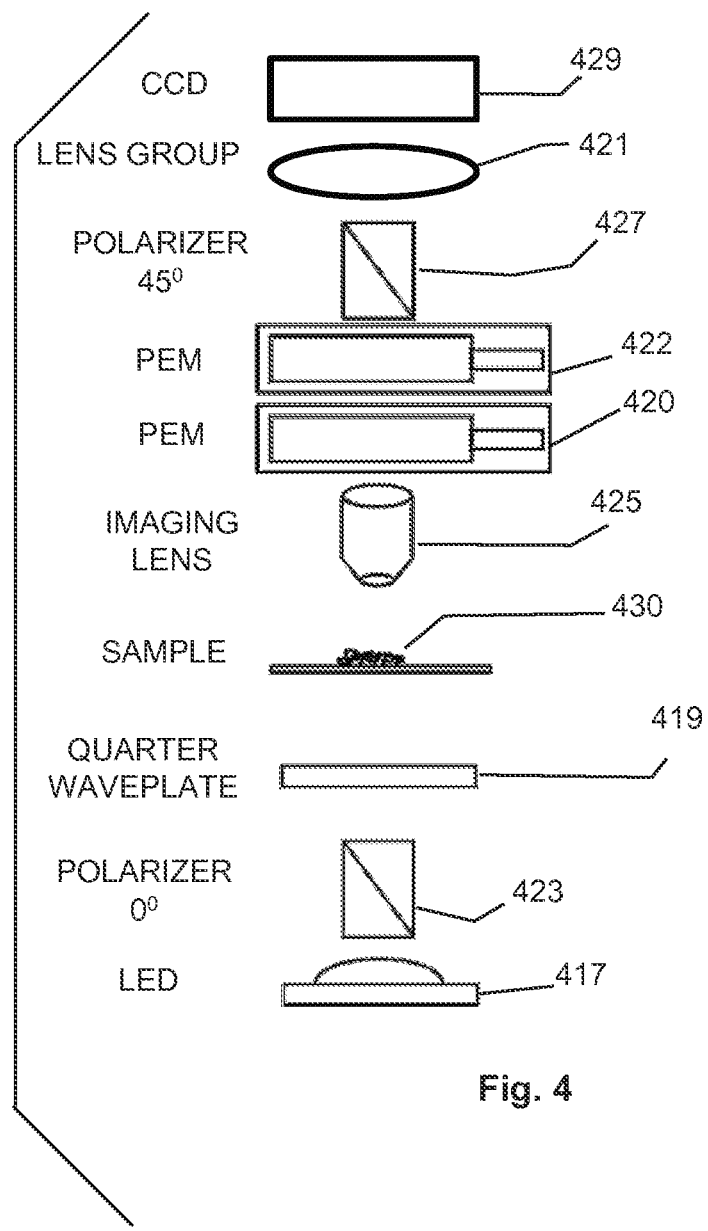
FIG. 4 is a diagram showing another preferred arrangement of the optical components of a system that may be used for imaging polarization properties, such as Stokes parameters, across an area of a sample.

FIG. 4 depicts an optical setup that is particularly useful for imaging Stokes parameters of a sample. That setup includes a light source 417 that directs light (upwardly in FIG. 4) through a sample 430 to an imaging device 429 such as a conventional CMOS or CCD-type camera. The light source is, preferably, an LED. The light from the source 417 passes through a polarizer 423 oriented at 45° relative to the baseline axis of the setup and a 0° quarter-waveplate 419 before passing through the sample 430 and an imaging lens 425.

The polarized light emanating from the imaging lens is incident upon the optical element of a first photoelastic modulator ("PEM") 420. The PEM 420 has its birefringent axis oriented at 0° and is controlled by an associated controller that imparts an oscillating birefringence to the optical element of the PEM, preferably at a nominal frequency of 42 kHz.

With continued reference to FIG. 4, the light emanating from the first PEM 420 is directed through a second PEM 422 that is controlled by an associated controller to operate at a modulation frequency (for example, 47 kHz when turned ON). The second PEM 422 is oriented at 45°. A second polarizer 427, oriented at 22.5°, and lens group 421 are between the second PEM 422 and the CCD 429.

The trigger pulses in this embodiment are selected at desired phases during a PEM modulation cycle. This is summarized in the following Table 1, Operation Mode 1, with the second PEM 422 turned OFF, and where pulses are triggered at four phases during a PEM cycle.

TABLE 1

| Operation Mode 1: Second PEM 422 Turned Off. | | | | |
|---|---|---|---|---|
| PEM (1$^{st}$, 42 kHz, π) Phase ($\omega_1$t) | 0, π | π/6 (30°). 5π/6 (150°) | π/2 | 7π/6 (210°), 11π/6 (330°) |
| $\delta_{42} = \pi\sin(\omega_1 t)$ | 0 | π/2 | π | −π/2 |
| $\sin(\delta_{42})$ | 0 | 1 | 0 | −1 |
| $\cos(\delta_{42})$ | 1 | 0 | −1 | 0 |

The camera intensity (detector) signal at each PEM phase becomes:

a. $\omega_1 t=0$, or π:

$$I_{42cp} = I_o\left[1 + \frac{\sqrt{2}}{2}\sin(2\theta_s)\sin(\delta_s) - \frac{\sqrt{2}}{2}\cos(2\theta_s)\sin(\delta_s)\right]$$

b. $\omega_1 t=\pi/6(30°)$, or 5π/6 (150°):

$$I_{42sp} = I_o\left[1 + \frac{\sqrt{2}}{2}\sin(2\theta_s)\sin(\delta_s) - \frac{\sqrt{2}}{2}\cos(2\theta_s)\right]$$

c. $\omega_1 t=\pi/2$:

$$I_{42cn} = I_o\left[1 + \frac{\sqrt{2}}{2}\sin(2\theta_s)\sin(\delta_s) + \frac{\sqrt{2}}{2}\cos(2\theta_s)\sin(\delta_s)\right]$$

d. $\omega_1 t=7\pi/6$ (210°), or 11π/6 (330°):

$$I_{42sn} = I_o\left[1 + \frac{\sqrt{2}}{2}\sin(2\theta_s)\sin(\delta_s) + \frac{\sqrt{2}}{2}\cos(\delta_s)\right]$$

A measurement taken without a sample in the setup will provide $I_0$. Combining terms (a)-(d) and normalizing to $I_0$ provide measurements of $\sin(2\theta_S)\sin(\delta_S)$, $\cos(2\theta_S)\sin(\delta_S)$, and $\cos(\delta)$, which are Mueller matrix elements $M_{13}$, $M_{23}$, and $M_{33}$. The linear retardance, $\delta_S$, and angle of the fast axis, $\theta_S$, are solved using the following equations.

$$\theta_S = \frac{1}{2}\tan 2^{-1}(M_{13}, M_{23})$$

$$\delta_S = \tan^{-1}\left(\sqrt{\left(\frac{M_{13}}{M_{33}}\right)^2 + \left(\frac{M_{23}}{M_{33}}\right)^2}\right)$$

Above, tan $2^{-1}$ is the four quadrant arc tangent.

As seen above, linear birefringence can be measured using a single PEM in this optical configuration. However, one of the three terms, $M_{13}$, is measured with a "DC" offset, which is more susceptible to measurement errors. This term can be more accurately measured at the second PEM's modulation frequency as summarized in the following Table 2, Operation Mode 2, with the first PEM 420 turned OFF, and where pulses are triggered at four phases during a PEM cycle.

TABLE 2

| Operation Mode 2: First PEM 420 Turned Off. | | | | |
|---|---|---|---|---|
| PEM (2nd, 4 kHz, π) Phase ($\omega_2$t) | 0, π | π/6 (30°). 5π/6 (150°) | π/2 | 7π/6 (210°), 11π/6 (330°) |
| $\delta_{47} = \pi\sin(\omega_2 t)$ | 0 | π/2 | π | −π/2 |
| $\sin(\delta_{47})$ | 0 | 1 | 0 | −1 |
| $\cos(\delta_{47})$ | 1 | 0 | −1 | 0 |

The camera intensity (detector) signal at each PEM phase becomes:

a. $\omega_2 t=0$, or π:

$$I_{47cp} = I_o\left[1 + \frac{\sqrt{2}}{2}\sin(2\theta_s)\sin(\delta_s) - \frac{\sqrt{2}}{2}\cos(2\theta_S)\sin(\delta_s)\right]$$

b. $w_2 t=\pi/6$ (30°), or 5π/6 (150°):

$$I_{47sp} = I_o\left[1 + \frac{\sqrt{2}}{2}\sin(2\theta_s)\sin(\delta_s) - \frac{\sqrt{2}}{2}\cos(\delta_s)\right]$$

c. $\omega_2 t=\pi/2$:

$$I_{47cn} = I_o\left[1 + \frac{\sqrt{2}}{2}\sin(2\theta_s)\sin(\delta_s) + \frac{\sqrt{2}}{2}\cos(2\theta_S)\sin(\delta_s)\right]$$

d. $\omega_2 t=7\pi/6$ (210°), or 11π/6 (330°):

$$I_{47sn} = I_o \left[ 1 + \frac{\sqrt{2}}{2}\sin(2\theta_s)\sin(\delta_s) + \frac{\sqrt{2}}{2}\cos(\delta_s) \right]$$

Combining terms (a) and (c) can provide measurements of $\sin(2\theta_S)\sin(\delta_S)$, which is Mueller matrix elements $M_{13}$, at the second PEM's modulation. The four pieces of data from both Operation Modes 1 and 2 are collected to improve signal-to-noise by averaging.

In view of the foregoing, the optical setup illustrated in FIG. 4 is amenable to three operation configurations: (1) Using only one PEM (a relatively lower cost/complexity option); (2) Using both PEMs but operated sequentially (Operation Modes 1 and 2 above); or (3) Operating both PEMs simultaneously. Selection of the appropriate configuration depends upon the time constraints (exposure time), power and wavelengths of source light used, and the field sizes and magnifications employed in a particular application.

Figure 5:
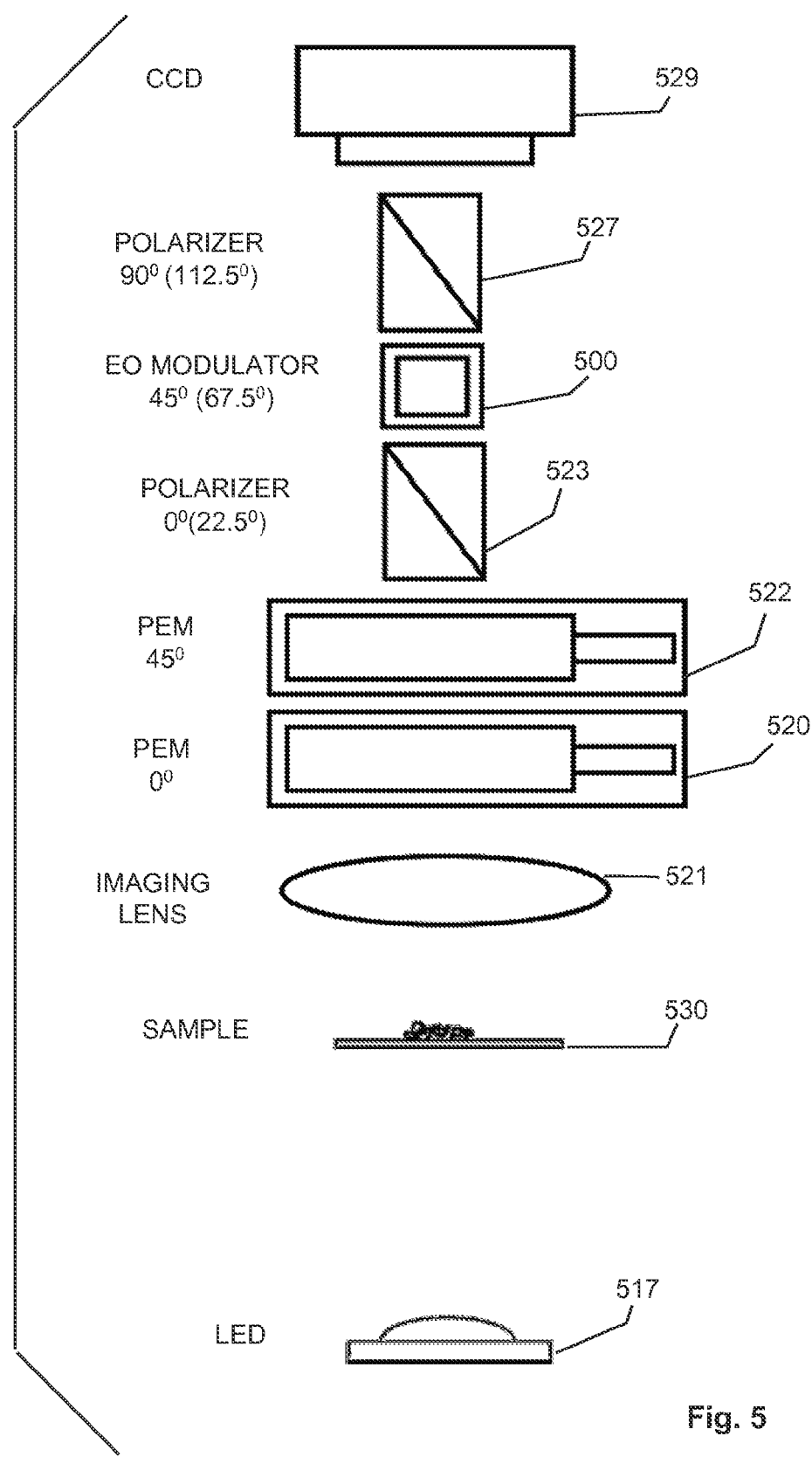
FIG. 5 is a diagram showing another preferred arrangement of the optical components of a system that may be used for imaging polarization properties.

FIG. 5 shows another embodiment of an optical setup that is also useful for imaging Stokes parameters and where an electro-optic modulator 500 provides rapid "gating" (sequentially permitting and occluding light transmission through the modulator) of the source light reaching the CCD. (Another option is to use a CCD intensifier in lieu of an electro-optic modulator.) Such an approach is an alternative to pulsing or strobing the source light as described above.

The instrument formed in accordance with the optical setup of FIG. 5 has two primary variations. In one configuration, the first polarizer 523 is aligned at 0°; in the other configuration, the polarizer is aligned at 22.5°. The intensity equation for the 0° configuration is given below.

$$I(\delta_1, \delta_2) = S_0 + C_{\delta 2} S_1 + S_{\delta 1} S_{\delta 2} S_3 - C_{\delta 1} S_{\delta 2} S_3$$

Where the Stokes vector is given by the following equation:

$$S = \begin{bmatrix} S_0 \\ S_1 \\ S_2 \\ S_3 \end{bmatrix}$$

The prior intensity equation can also be written in vector form.

$$I(\delta_1, \delta_2) = \begin{bmatrix} 1 & C_{\delta 2} & S_{\delta 1} S_{\delta 2} & -C_{\delta 1} \delta_2 \end{bmatrix} \begin{bmatrix} S_0 \\ S_1 \\ S_2 \\ S_3 \end{bmatrix}$$

The vector formed from the state of the modulators can be given the name of the analyzer vector as above. For the configuration with the polarizer at 22.5°, the analyzer vector is given below.

$$A(\delta_1, \delta_2) = \begin{bmatrix} 1 & \frac{\sqrt{2}}{2} C_{\delta 1} + \frac{\sqrt{2}}{2} S_{\delta 1} S_{\delta 2} & \frac{\sqrt{2}}{2} C_{\delta 2} & \frac{\sqrt{2}}{2} C_{\delta 1} S_{\delta 2} - \frac{\sqrt{2}}{2} S_{\delta 1} \end{bmatrix}$$

This configuration may be operated with each modulator alternating between ON and OFF because all the quantities of interest can be expressed as the harmonics of only one PEM. If the first modulator is turned off, the equation for the analyzer vector is given below.

$$A(0, \delta_2) = \begin{bmatrix} 1 & \frac{\sqrt{2}}{2} & \frac{\sqrt{2}}{2} C_{\delta 2} & \frac{\sqrt{2}}{2} S_{\delta 2} \end{bmatrix}$$

And likewise, the analyzer vector with the second modulator turned off is given below.

$$A(\delta_1, 0) = \begin{bmatrix} 1 & \frac{\sqrt{2}}{2} C_{\delta 1} & \frac{\sqrt{2}}{2} & \frac{\sqrt{2}}{2} S_{\delta 1} \end{bmatrix}$$

The drive electronics for such a system are considerably simpler as the pulse scheme described above only depends upon the currently active modulator.

By choosing to use the LED illumination as discussed above, this system can also be used to measure the linear birefringence of a sample as well as the linear extinction. The particulars of such an instrument are discussed next with reference to FIG. 6.

Figure 6:
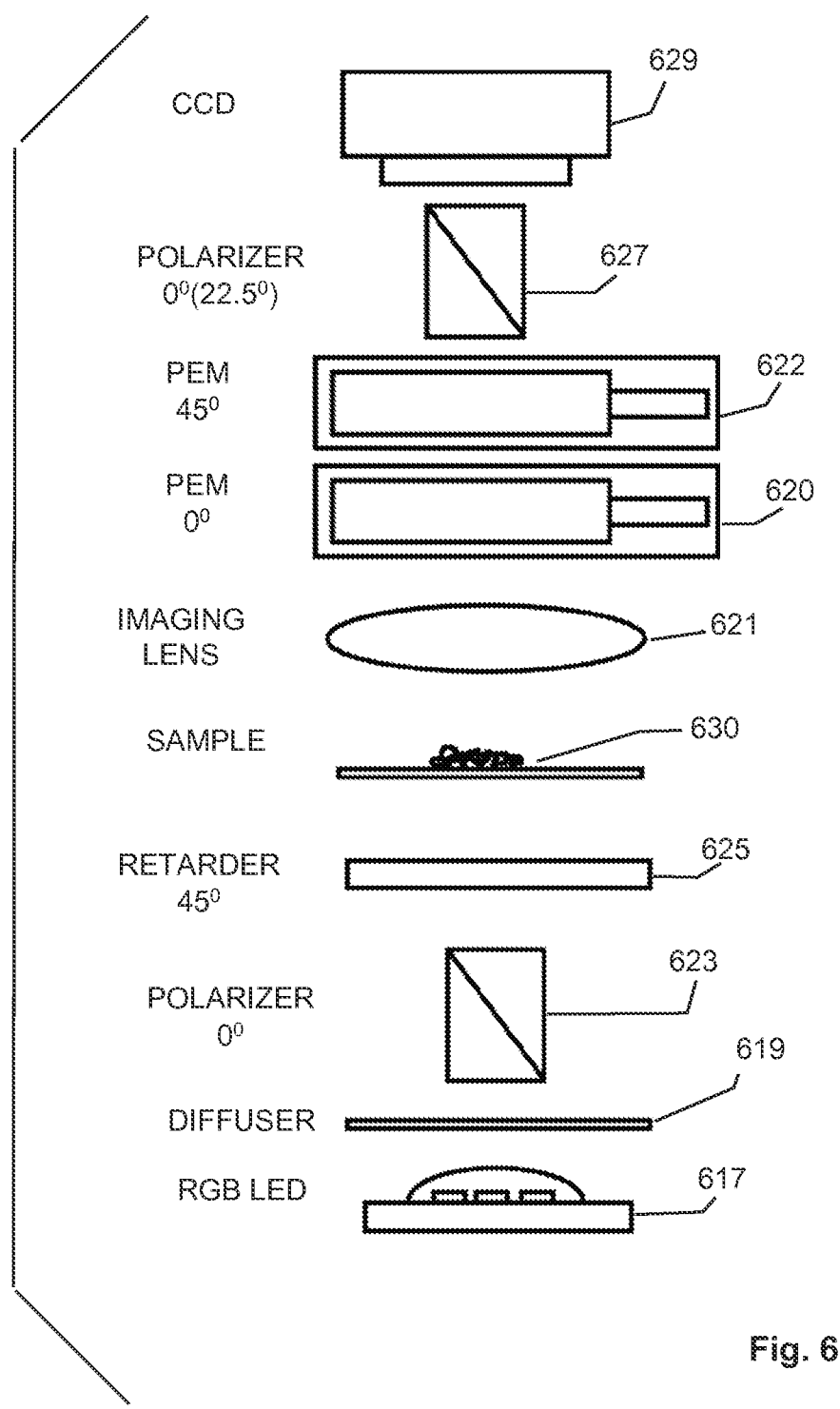
FIG. 6 is a diagram showing another preferred arrangement of the optical components of a system that may be used for imaging polarization properties such as differential extinction.

In the embodiment of FIG. 6, the retarder 625 is, ideally, a perfect achromatic quarter-waveplate and, in combination with the 0° polarizer 623, illuminates the sample with perfectly circularly polarized light. This Stokes polarimeter can measure the Stokes vector after the sample 630 as discussed above. To measure the birefringence or linear extinction, the Mueller matrix of the first half of the instrument is given below.

$$M_{SOT} = M_S M_{ret}\left(\frac{\pi}{4}, \frac{\pi}{2}\right) M_{pol}(0)$$

By isolating the first column of the resulting Mueller matrix, the Stokes vector contains all the relevant information to solve for the retardance and angle of the fast axis as above.

$$S = \begin{bmatrix} 1 \\ -S_\delta S_\theta \\ S_\delta C_\theta \\ C_\delta \end{bmatrix} = \begin{bmatrix} M_{00} \\ M_{13} \\ M_{23} \\ M_{33} \end{bmatrix}$$

The trouble with this setup (FIG. 6) is that the retarder producing circularly polarized light is rarely purely achromatic. This results in the following Stokes vector after the sample.

$$S = \begin{bmatrix} M_{00} \\ C_{ret\delta} M_{11} + S_{ret\delta} M_{13} \\ C_{ret\delta} M_{12} + S_{ret\delta} M_{23} \\ -C_{ret\delta} M_{13} + S_{ret\delta} M_{33} \end{bmatrix}$$

In the equation above, $C_{ret\delta}$ is the cosine of the retardance of the waveplate and $S_{ret\delta}$ is the sine of the retardance of the waveplate 625. This can be somewhat corrected by measuring the Stokes vector of the retarder alone. Assuming perfect alignment, the Stokes vector of the retarder alone is given below.

$$S = \begin{bmatrix} 1 \\ C_{ret\delta} \\ 0 \\ S_{ret\delta} \end{bmatrix}$$

If the light source 617 is unpolarized, and the sample 630 exhibits differential extinction, then a Stokes polarimeter setup can also measure these properties. The polarizer 623 and retarder 625 are removed from the optical train, and the measured Stokes vector is given below.

$$S = \begin{bmatrix} T \\ -LE \\ -LE' \\ CE \end{bmatrix} = \begin{bmatrix} M_{00} \\ M_{10} \\ M_{20} \\ M_{30} \end{bmatrix}$$

Where T is the transmission, LE is the linear extinction along 0°/90°, LE' is the linear extinction along 45°/135°, and CE is the circular extinction.

It is noteworthy here that the amplitude of modulation and phase lag between the detected square wave from the photoelastic modulators 620, 622 and the actual retardance both need to be calibrated. The complete equation for the amplitude of the birefringence at any time is given below.

$$\delta(t, A, \phi) = A\cos(2\pi ft + \phi)$$

In the equation above, $\phi$ is the phase lag, f is the frequency of modulation, t is the time, A is the amplitude of modulation. The intensity measured at the CCD 629 is proportional to the sine and/or cosine of the retardance of each modulator, $\delta(t, A, \phi)$.

$$C_\delta = \cos(\delta(t, A, \phi)) = \cos(A\cos(2\pi ft + \phi))$$

$$S_\delta = \sin(\delta(t, A, \phi)) = \sin(A\cos(2\pi ft + \phi))$$

The light source 614 for the optical train is only on during certain times, and the intensity at the CCD 629 is thereby taken as the average of the sine or cosine of the birefringence during this time.

$$C_\delta \cong \frac{\int_{t=t_1}^{t_2} \cos(A\cos(2\pi t + \varphi))}{t_2 - t_1}$$

More practically, the mean of the sine or cosine can be taken as the mean over only a few discrete points during the ON time.

While the pulsing, triggering and gating techniques described above are conceptually straightforward, the poor exposure time to intensity ratio can induce considerable dark current and light pollution noise. In order to alleviate this, frequency synthesis can be utilized to generate a simple waveform at the higher harmonics of interest. This approach is described in detail following discussion of a system for simultaneous imaging of both in-plane and out-of-plane birefringence properties of a sample over a wide range of incidence angles.

Figure 7:
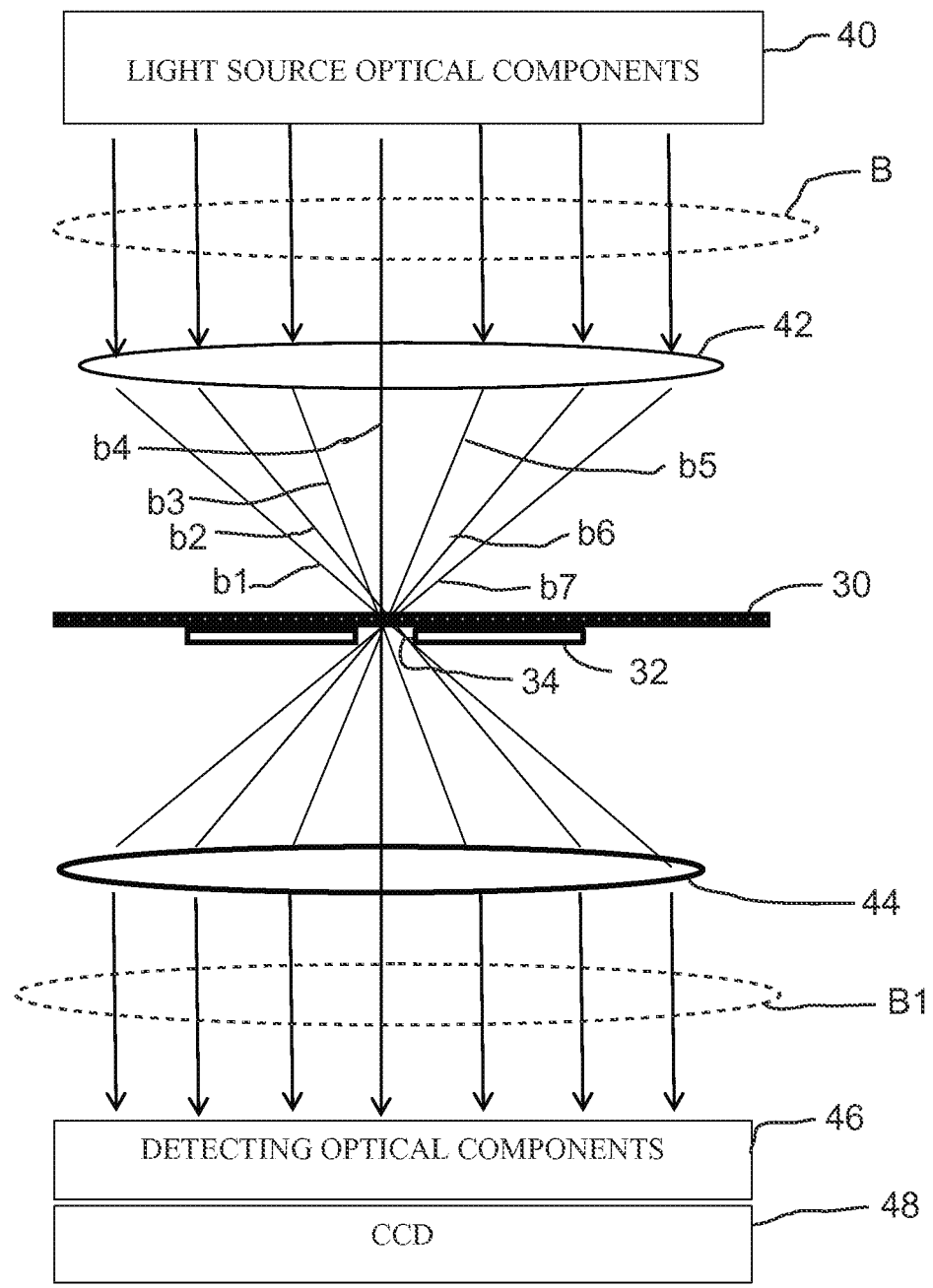
FIG. 7 is a diagram of a preferred arrangement of the optical components of a system for simultaneously imaging both in-plane and out-of-plane birefringence properties of a sample.

FIG. 7 is a diagram showing a preferred arrangement of the optical-train components of a system for simultaneous imaging of both in-plane and out-of-plane birefringence properties of a sample over a wide range of incidence angles. In FIG. 7, there is shown an optical sample 30, which may be, for example, a thin polymeric film intended for use as a birefringence compensation film as discussed above. The sample is supported upon a holder 32 with an associated variable aperture 34.

The system includes light source optical components 40, the particulars of which are described further below. Those components 40 produce a source beam "B" of polarization-modulated, collimated light. That beam "B" is directed through a focusing lens system 42 that has an aperture-to-focal-length ratio selected for focusing the light on the sample 30 such that the individual rays "b1-b7" that reach a location on the sample 30 each arrive with a different angle of incidence. For illustration purposes, an exemplary batch of only seven such rays "b1-b7" is shown in FIG. 7.

The incidence angle of the central ray "b4" is 0° or "normal" to the surface of the sample. The remaining rays "b1-b3" and "b5-b7" have incrementally larger incidence angles in the direction away from the normal, central ray "b4" and thus cover a wide range of incidence angles. The range can be determined by the selection of the focusing lens system and dependent upon, for example, the sought-after viewing angle of the device with which the compensation film is to be employed.

The variable aperture 34 (which can be located as shown or, alternatively, between the sample 30 and lens system 42) is adjusted to facilitate accurate control of the generation of the range of incidence angles.

The rays "b1-b7" that emanate from the sample are directed through a collimating lens system 44 that directs that collimated beam "B1" through detecting optical components 46 (further described below) to a multi-pixel imaging device 48. In a preferred embodiment, that device may be a digital imaging device or camera that employs an intensified, charge-coupled device (ICCD), a standard CCD, or CMOS-type sensor. For convenience, the imaging device will be hereafter referred to as a CCD 48.

Figure 8:
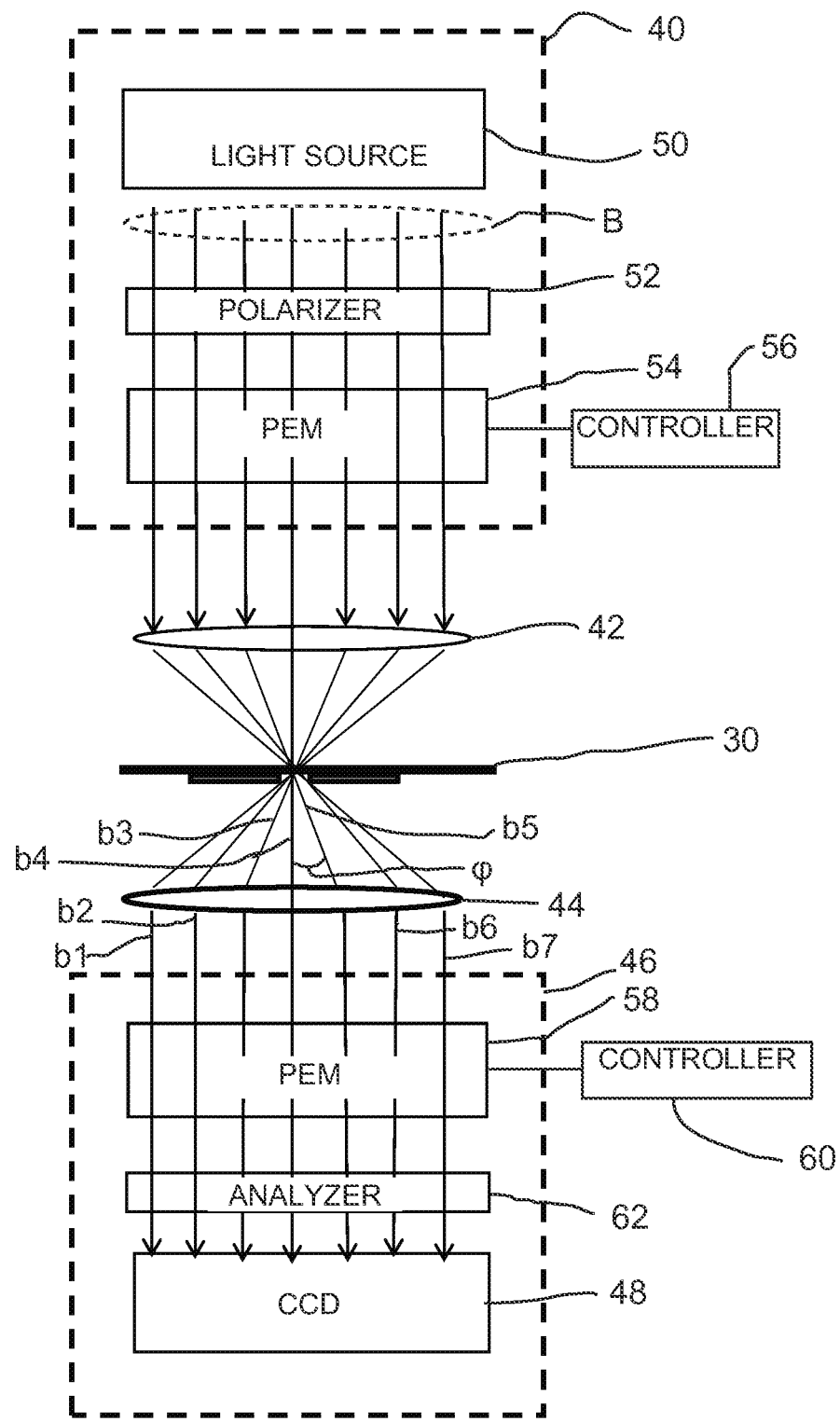
FIG. 8 is a diagram like FIG. 7, but illustrating the particulars of the light source and detecting optical components of the system.

With reference to FIG. 8, in one preferred embodiment, the light source optical components 40 include a light source 50, such as a light emitting diode (LED), with associated lensing for generating the source beam "B." The beam "B" passes through a polarizer 52 that is oriented with its polarization direction at +45° relative to a baseline axis. A high-extinction polarizer, such as a Glan-Thompson calcite polarizer, is preferred.

The polarized light emanating from the polarizer 52 is incident upon the optical element of a first photoelastic modulator ("PEM") 54. In a preferred embodiment, the PEM is one manufactured by Hinds Instruments, Inc., of Hillsboro, Oregon. It is noteworthy here that although a PEM is preferred, other mechanisms could be used for modulating the polarization of the source light.

The most accurate birefringence measurements are achieved when one minimizes the residual birefringence present in the optical components of the system. To this end, the PEM 54 is configured to eliminate residual birefringence that may be otherwise produced by the forces present in supporting the optical element of the PEM.

The PEM 54 has its birefringent axis oriented at 0° and is controlled by a controller 56 that imparts an oscillating birefringence to the optical element of the PEM, preferably at a nominal frequency of 50 kHz. In this regard, the controller 56 drives one or more quartz transducers that are adhered to the optical element of the PEM.

The oscillating birefringence of the PEM 54 introduces a time-varying phase difference between the orthogonal components of the polarized light that propagates through the PEM. At any instant in time, the phase difference represents the retardation introduced by the PEM. As noted earlier, the retardation is measurable in units of length, such as nanometers. The PEM is adjustable to allow variation of the amplitude of the retardation introduced by the PEM, as described more below.

With continued reference to FIG. 8, the detecting optical components 46 include a second PEM 58 that is controlled by a controller 60 to operate at a modulation frequency (for example, 55 kHz) that is different from the modulation frequency of the first PEM 54. The second PEM 58 is oriented at 45°. An analyzer 62, oriented at 0°, is between the second PEM 58 and the CCD 48.

The CCD 48 includes individual pixels, each of which receives the light from a ray "b1-b7". Thus, the light intensity captured in each pixel corresponds to the birefringence characteristics of a ray having a given angle of incidence such that, for example, a central pixel in the CCD would receive light intensity information relating to a ray "b4" at a normal incidence, and a pixel aligned with ray "b7" would receive light intensity information relating to a ray having the greatest angle of incidence.

The preferred CCD 48 includes a gain mask that is controlled by a computer or dedicated controller operated by a computer. The CCD 48 is a time-gated device having a temporal resolution or frame rate that is generally an order of magnitude slower than the frequency with which the PEMs 54, 58 are driven. As mentioned above, if operated normally, the CCD would, in each frame, average out the PEM-modulated light received in each pixel and thus render impossible the ability to calculate the birefringence properties of interest (here, the in-plane and out-of-plane birefringence).

Described below is an innovative technique for triggering the gating of the CCD 48 in a manner that allows rapid collection of a useful amount of light information in instances only when the modulation state of both PEMs 54, 58 is known, thereby enabling the precise, simultaneous determination of in-plane and out-of-plane birefringence properties of the sample corresponding to each pixel of the CCD, hence over a wide range of incidence angles.

Before describing the CCD gating technique just mentioned, this description proceeds with a delineation of the data analysis applied to the intensity information received in each pixel on the assumption that the triggered CCD pixel information collected is processed (demodulated) to yield only the relevant intensity information for each pixel. (It is noteworthy that each angled apart light ray "b1-b7" experiences a slightly different polarization effect from the lenses and other optical components of the system. Accordingly, as a preliminary step, each pixel must be offset or calibrated to correct for the effect.)

The thin film material, such as the sample 30 of interest here, typically has polymeric structure such that the normal birefringence or in-plane birefringence is significantly less than the vertical or out-of-plane birefringence. That is, $n_X \approx n_Y \neq n_Z$, where $n_Y$ and $n_X$ are, respectively, the indices of refraction of the sample in the orthogonal axes, X and Y, and $n_Z$ is the index of refraction of the sample that is normal to the plane defined by those X and Y axes.

Data Analysis: Normal Retardation (in-plane retardation): The quantity $\delta_N$ represents the magnitude of the normal retardation, in nanometers, that is measured at the normal incidence. The normal or in-plane birefringence is defined as:

$$\Delta n_N = n_Y - n_X$$

If the fast axis of the in-plane birefringence is oriented at $\rho_N$, $n_Y > n_X$ where X coincides with the fast axis orientation, the normal retardation and normal birefringence is as follows:

$$\delta_N = \Delta n_N \cdot d \cdot 1000 = (n_Y - n_X) d \cdot 1000 \text{ or} \qquad \text{eqn. (1)}$$

$$\Delta n_N = n_Y - n_X = \frac{\delta_N}{d \cdot 1000}$$

where d is the thickness of the thin film in micrometers.

Oblique retardation: The quantity $\delta_O$ represents the magnitude of oblique retardation, in nanometers, that is measured at an oblique incident angle ($\phi$), which is the angle (see FIG. 8) between the oblique and normal beams. If the sample has an average index of refraction of n, the incident angle inside the film sample is:

$$\theta = \sin^{-1}\left[\frac{\sin\varphi}{n}\right] \qquad \text{eqn. (2)}$$

For the oblique incidence, the ordinary and extraordinary rays will have different indices of refraction inside the film sample, as in a uniaxial crystal. The refractive index of the ordinary ray, $n_o$, is independent of the incidence angle, while the refractive index of the extraordinary ray is dependent on the incidence angles. The extraordinary ray in the case here is polarized in the XZ plane (E-vector vibrating in the XZ plane) and the ray has an angle of θ to the Z-axis (optic axis). The effective refractive index, $n_{eff}$, of the extraordinary ray is:

$$n_{eff}(\theta) = \frac{n_o n_e}{\sqrt{n_e^2 \cos^2\theta + n_o^2 \sin^2\theta}} \qquad \text{eqn. (3)}$$

where $n_e = n_Z$ and $n_o = n_X$, $n_Y$ (uniaxial crystal). The $n_{eff}$ is always between and $n_e$ and $n_o$.

Vertical (out-of-plane) birefringence calculation: When $n_Z < n_X \approx n_Y$, $n_{eff} < n_Y$, the measured fast axis of the oblique retardation will appear to be along the X-axis. The oblique retardation in the XZ plane can be expressed as follows:

$$\delta_O\left[n_Y - \left(\frac{n_X n_Z}{\sqrt{n_Z^2 \cos^2\theta + n_X^2 \sin^2\theta}}\right)\right] \cdot \frac{d \cdot 1000}{\cos\theta} \qquad \text{eqn. (4)}$$

Rearranging equation (4) and using eqn. (1) yields:

$$\frac{\delta_O \cos\theta}{d \cdot 1000} - \frac{\delta_N}{d \cdot 1000} = n_X - \left(\frac{n_X n_Z}{\sqrt{n_Z^2 \cos^2\theta + n_X^2 \sin^2\theta}}\right) \qquad \text{eqn. (5)}$$

which leads to $$\frac{\delta_O \cos\theta}{d \cdot 1000} - \frac{\delta_N}{d \cdot 1000} \approx (n_X - n_Z)\sin^2\theta = \text{Sign}(VBR)(n_Z - n_X)\sin^2\theta \qquad \text{eqn. (6)}$$

or,

-continued $$\Delta n_V = \text{Sign}(VBR)(n_Z - n_X) = \frac{1}{d \cdot 1000 \cdot \sin^2\theta}(\cos\theta \cdot \delta_O - \delta_N) \quad \text{eqn. (7)}$$

where Sign (VBR)=−1 when nz<nx.

Note that the approximation used from equations. (5) to (6) is very good for small Δn. At Δn=nx−nz=0.01, the approximation has less than 1% error.

$R_{th}$ calculation: When $n_z < n_x \approx n_y$, the $R_{th}$ (out-of-plane retardance) is defined as follows:

$$R_{th} = \left| n_Z - \frac{(n_X + n_Y)}{2} \right| d \times 1000 \quad \text{eqn. (8)}$$

$$= \left[ \frac{(n_X + n_Y)}{2} - n_Z \right] d \times 1000$$

$$= \left( \Delta n_V + \frac{\Delta n_N}{2} \right) d \times 1000$$

In terms of experimental measurements, we have:

$$R_{th} = \frac{1}{\sin^2\theta}(\cos\theta \cdot \delta_O - \delta_N) + \frac{\delta_N}{2} \quad \text{eqn. (9)}$$

In equation (9), the thickness of the film does not enter the calculation of $R_{th}$ from the measured normal and oblique retardation values because the measured retardation values have an implicit thickness.

This description now turns to the above-mentioned technique for triggering the gating of the CCD 48 in a manner that allows rapid collection of a useful amount of light information and in instances only when the modulation state of both PEMs 54, 58 is known, thereby enabling the precise determination of birefringence properties of the sample that correspond to each pixel of the CCD.

In particular, this technique employs frequency synthesis for generating a simple waveform at high harmonics of the PEM modulations for gating the CCD. This approach is best understood by first considering a system where the optical train includes only a single PEM (with the understanding that using only a single PEM severely limits the range of optical properties that can be measured) and then returning to consideration of the frequency synthesis approach in systems using two or more PEMs.

Frequency synthesis for controlling an imaging system that uses a single PEM can employ a standard half duty square waveform. Such waveforms are simple to create, and allow for the maximum light throughput to the imaging device. Use of such a waveform, however, requires careful attention to details such as the expected intensity difference between two images (the response), and the phase of the PEM. The first issue that needs to be addressed is how to predict the expected intensity from a square-wave-gated CCD and the Bessel waveform that is generated by the PEM.

The expected response for a half duty square wave combined with a Bessel waveform can be calculated by first multiplying the Fourier expansion of a square wave with the Fourier expansion for the Bessel waveform produced by the PEM. Shown below is the Fourier expansion of the Bessel waveform.

$$\cos[A\cos\omega] = J_0(A) + 2\sum_{n=1}^{\infty}(-1)^n J_{2n}(A)\cos[2n\omega] \quad \text{eqn. (10)}$$

$$\sin[A\cos\omega] = -2\sum_{n=1}^{\infty}(-1)^n J_{2n-1}(A)\cos[(2n-1)\omega] \quad \text{eqn. (11)}$$

Below is the Fourier expansion of the half duty square wave.

$$\frac{4}{\pi}\sum_{n=1}^{\infty}\frac{\sin[(2k-1)\omega]}{2k-1} \quad \text{eqn. (12)}$$

The expected correlation response between any two waveforms is shown below.

$$R = \frac{\int_{t=0}^{T} A(t)M(t)dt}{\int_{t=0}^{T} M(t)^2 dt} \quad \text{eqn. (13)}$$

where R is the expected scalar response of the acquired waveform, A(t, in this case, a Bessel waveform; and M(t) is the modulating waveform, a half duty square wave. If the phase between the Bessel waveform and the square wave is assumed to be zero, then the equation above can be solved as the expansions below.

$$R_{\cos(\delta)} = \sum_{n=1}^{\infty}(-1)^n \frac{8}{(2n-1)\pi} J_{2(2n-1)}(A) \quad \text{eqn. (14)}$$

$$R_{\sin(\delta)} = \sum_{n=1}^{\infty}\frac{8}{(2n-1)\pi} J_{2n-1}(A) \quad \text{eqn. (15)}$$

In the equations above, the square wave of the cosine response is double the base Bessel waveform frequency, and the sine response frequency is the same as the Bessel waveform frequency. Using the two equations (14, 15) above, the expected response of a Bessel waveform can be predicted, and utilized to solve for the optical properties of the sample. To accomplish this, two images are collected for every Bessel waveform term (the cosine or sine in this case). The difference between these two images is directly correlated to the Mueller matrix elements that describe the optical properties of the sample.

Figure 9:
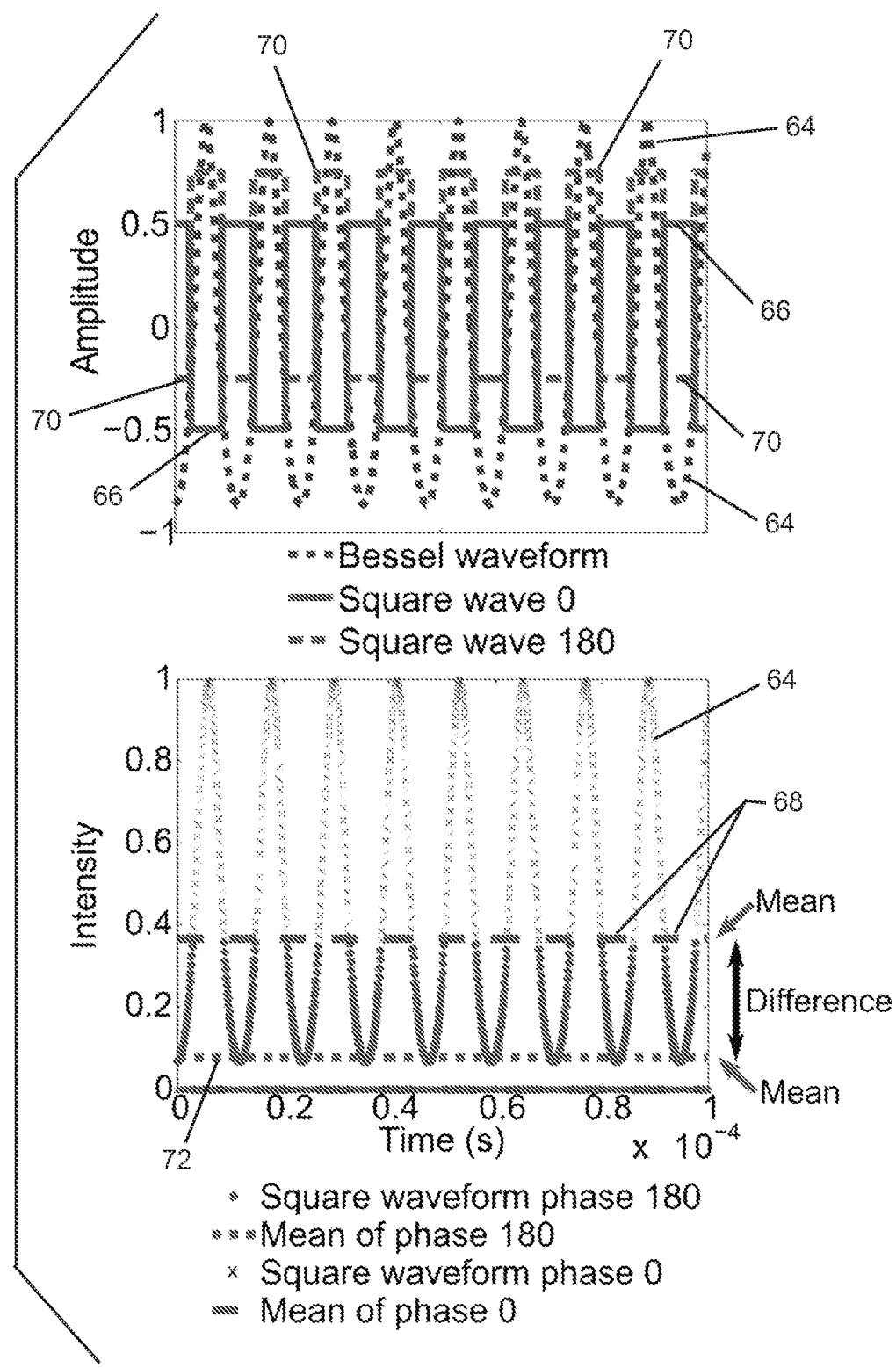
FIG. 9 is a diagram showing the relationship between the Bessel waveform generated by a PEM and a half duty square wave generated as part of a gating trigger signal for the imaging device of the present system.

As shown in the graphs of FIG. 9, the Bessel waveform 64 is assumed to be a pure cosine Bessel waveform. First, a square wave 66 with twice the frequency and no phase offset is generated. The mean intensity 68 is measured using an integrating intensity detector. Then the square wave is phase shifted 70 by half a wave and a second mean intensity measurement 72 is taken. The difference in intensity between these two measurements is given as the response in the equations (13)-(15) above.

In the following portion of this description, the effects of using multiple PEMs and frequency synthesis are described primarily with reference to the block diagram of FIG. 10. The initial step is to generate a square wave at any given harmonic of the PEMs with the correct phase.

When using half duty square waves with multiple PEMs in simultaneous operation, the mixed harmonics of the PEMs must be synthesized. The synthesis can most easily be accomplished with modern digital hardware. The first step in the synthesis is to measure and record in, for example, computer memory (FIG. 10, 401) the period of each PEM 54, 58 present in the optical setup, here the setup shown in FIG. 8.

To measure the period of each PEM, the PEM's feedback or output square wave is measured using a high-frequency counter. The counter is selected to operate at orders of magnitude higher than the PEM in order to attain the necessary frequency accuracy. For instance, a 400 MHz counter applied to a 40 kHz PEM will have ten thousand counts per cycle for a resolution of 4 Hz. To increase this resolution, multiple PEM cycles are measured.

To ensure that the synthesized frequency does not contribute noise to the PEM instrumentation, the frequency resolution needs to be lower than 0.1 Hz. To attain this resolution for the example just given, at least 40 complete PEM cycles must be measured and averaged with a 400 MHz counter clock or 80 complete cycles with a 200 MHz counter clock. For ease of implementation, measuring powers of two cycles allows for simple right-shift division. So for a 200 MHz counter clock and 40 kHz PEM, 128 PEM cycles are averaged ($2^7$) with the counter containing a total of at least 20 bits. For a 200 MHz counter clock and a 60 kHz PEM, 256 PEM cycles ($2^8$) are averaged with a counter containing at least 20 bits total.

Once the period for each PEM is measured, the frequency can be calculated by simply inverting the period.

$$F = \frac{1}{P} \quad \text{Eqn. (16)}$$

Figure 10:
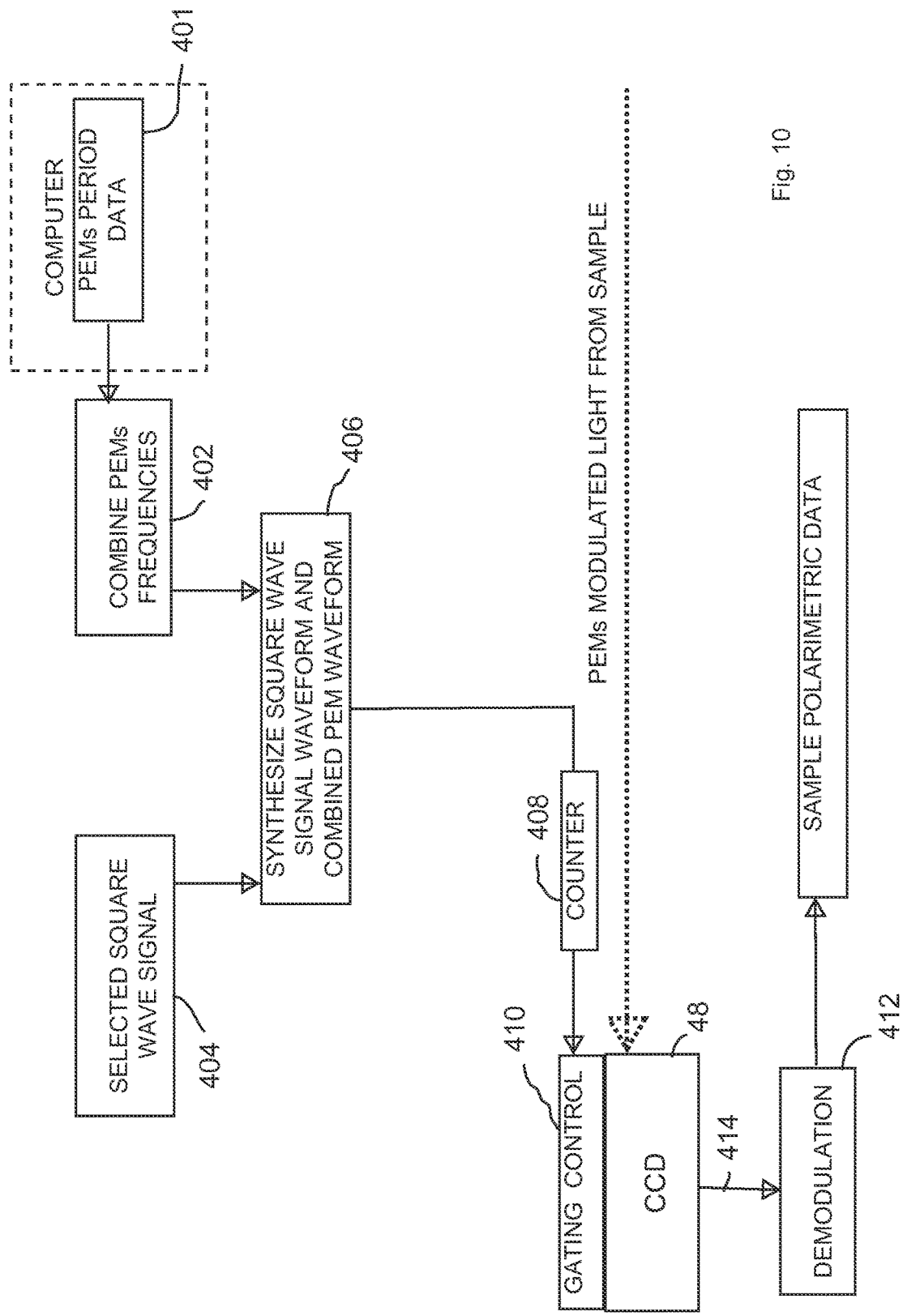
FIG. 10 is a diagram illustrating the steps employed for generating a frequency synthesized trigger signal for the gated imaging device of the present system.

The harmonic of interest can now be calculated by multiplying, then summing, the relevant frequencies (FIG. 10, 402). For instance, when using two PEMs operating at a frequency of $1F_1$ and $1F_2$, the cosine of the sample's birefringence is measured by examining the $1F_1+1F_2$ harmonic.

The period for the selected square wave (FIG. 10, 404) to be synthesized with the combined PEMs waveform (FIG. 10, 406) is then calculated by inverting its frequency. The resultant period is applied to another counter (FIG. 10, 408) that controls the output of gating control 410 of the CCD 48.

Given the forgoing generation and application of the frequency synthesized trigger signal as just discussed, upon demodulation (FIG. 10, 412) of the CCD output signal 414 as discussed below, the data received for each pixel of the CCD will correspond to known states of the PEMs that modulate the polarization of the beams involved and thus provide data that can be used to accurately calculate the birefringence measure of interest.

Figure 11:
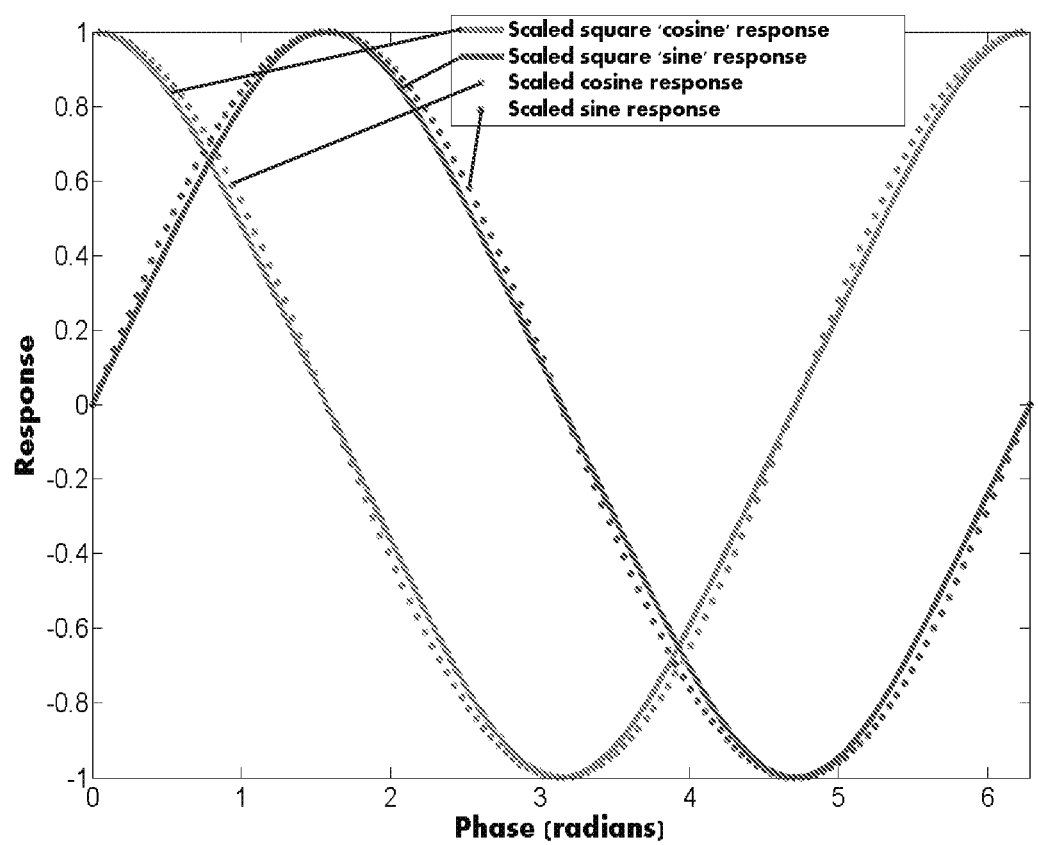
FIG. 11 is a diagram illustrating the harmonic relationship of a sine/cosine demodulating signal as compared to a measured square-wave demodulating signal for a single PEM system.

The phase of the CCD output signal 414 must be discerned for accurate demodulation (FIG. 10, 412) of that signal to extract the intensity information. With the use of a single PEM, the phase relationship between the PEM's Bessel waveform and a sine/cosine demodulating signal has the expected harmonic relationship, in that the angle between the sine and cosine directly allows for the calculation of the phase of the PEM. This is not the case, however, as here, for a system using square wave demodulation. With square wave demodulation, the higher harmonics of the square waves interact with the higher harmonics of the Bessel waveform, and the expected clean trigonometric relationship is polluted. For one PEM, the expected sine/cosine trigonometric relationship and the measured square wave response are graphed in FIG. 11.

The differences between the square wave response and sine/cosine response with phase can be approximated as below.

$$E_{cos} \cong \frac{1}{4\pi}[-\cos\varphi + \cos(3\varphi)] \quad \text{eqn. (17)}$$

$$E_{sin} \cong \frac{1}{4\pi}[\sin\varphi + \sin(3\varphi)] \quad \text{eqn. (18)}$$

$$\varphi = \varphi_B - \varphi_S \quad \text{eqn. (19)}$$

In equation (19), $\phi_B$ is the phase of the Bessel waveform and $\phi_S$ is the phase of demodulating square waveform. Of important note is that the square wave and sine/cosine waveform response is identical when the phase difference is zero or multiples of $\pi/2$. Accordingly, if the square wave can be generated with no difference in phase relation, then the simple analytical equations herein can be used.

In order to accomplish the demodulation without having to take these phase complications into account, the synthesized square wave must possess a zero phase relation to the basis Bessel waveforms. This zero phase relationship can be accomplished by starting the square waveform with an instantaneous phase offset:

$$\phi_O = N_1\phi_1 + N_2\phi_2 + \ldots \quad \text{eqn. (20)}$$

In the equation (20) above, $N_n$ is the harmonic multiple for each PEM (usually 1 or 2), and $\phi_n$ is the instantaneous phase. In practice, the instantaneous phase for each PEM is the counter used to measure the frequency. Accordingly, the total phase offset, $\phi_O$, will generally be much greater than the period of the generated frequency. As such, the phase offset must be reduced an arbitrary number of periods until it is below a single period but greater than zero. Then the frequency synthesis counter (FIG. 10, 408) is started from this value. Such a routine allows for the determination of both the frequency and phase of the square wave with reference to the Bessel waveforms generated from the PEMs.

Figure 12:
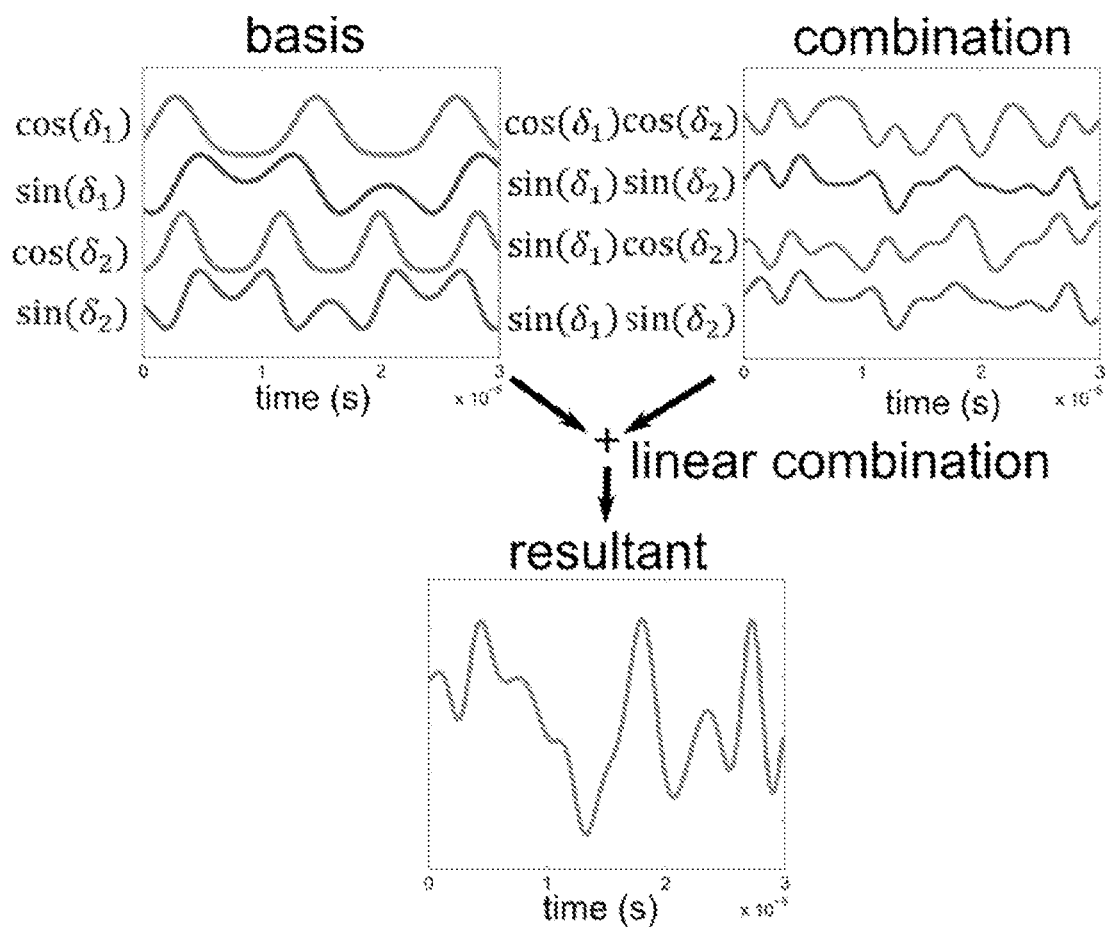
FIGS. 12 and 13 are diagrams illustrating how the Bessel waveforms of two or more PEMs are combined for arriving at a correct amplitude for driving the PEMS for well-conditioned demodulation of the output signal from the imaging device.

Next, the amplitude of modulation must be chosen to allow the separation and measurement of the Bessel waveforms from the total waveform. When using more than one PEM, the total waveform is the linear combination of basis Bessel waveforms and their combinations as shown in FIG. 12.

Mathematically, this situation can be presented as a matrix problem:

$$\begin{bmatrix} I_{2F_1} \\ I_{1F_2} \\ \vdots \\ I_{2F_1+2F_2} \\ \vdots \\ I_{2F_1+1F_2} \end{bmatrix} = R \begin{bmatrix} \cos(\delta_1) \\ \sin(\delta_1) \\ \vdots \\ \cos(\delta_1)\cos(\delta_2) \\ \vdots \\ \cos(\delta_1)\sin(\delta_2) \end{bmatrix} \quad \text{eqn. (21)}$$

In equation (21), $I_{NF_P}$ represents the measured intensity of one measurement of the gating at the synthesized frequency, or the difference of intensity measurements with a gating frequency at the given harmonic. The goal is then to invert the matrix, R, to solve for the amplitudes of each of the Bessel waveform harmonics given a number of intensity measurements. For best results, the matrix R must be invertible and well-conditioned. The optimal condition for matrix R occurs when the absolute value of the Bessel functions at the measured harmonics are equal. In the case of measuring the first and second harmonic in the preferred embodiment, $|J_1(A)|=|J_2(A)|$, this equivalence occurs at a driving amplitude for the PEMs of about 2.63 radians.

Figure 13:
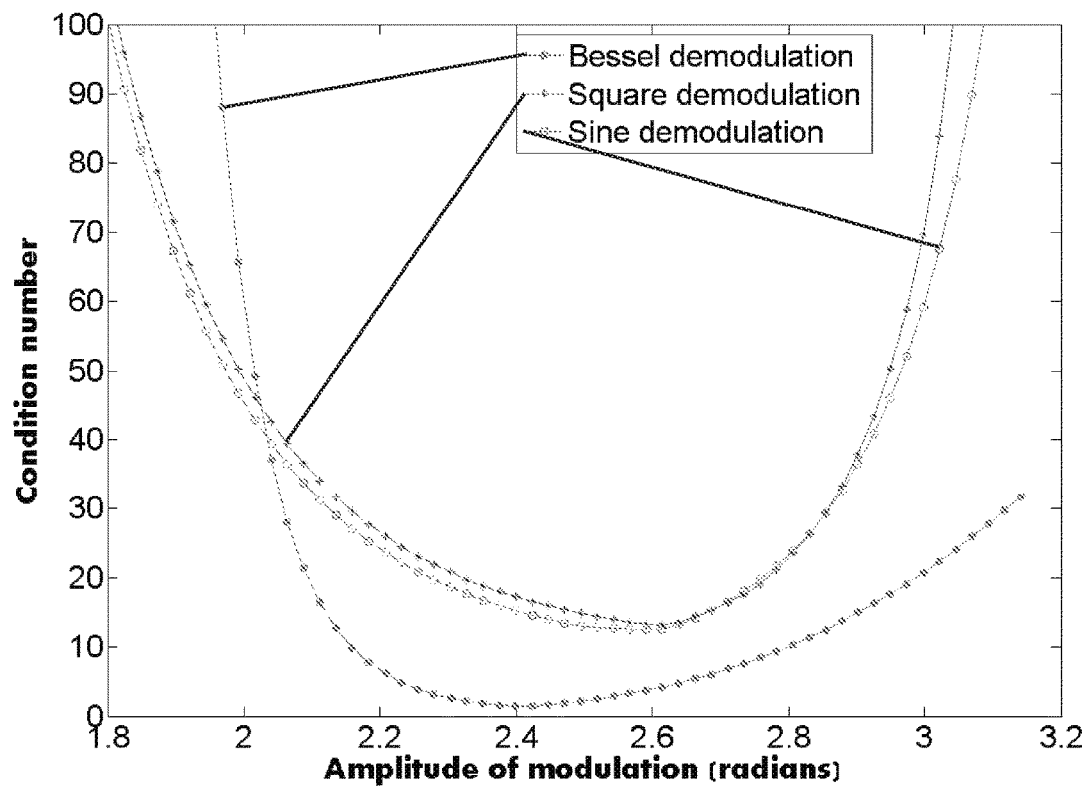

An illustrative plot of the condition number of a matrix R for a range of driving amplitudes is shown in FIG. 13 for a system that employs 4 PEMs (polarimeter) using three demodulation waveforms: Bessel, sine/cosine, and square. The best condition is found using Bessel waveform demodulation at the $J_0(A)=0$ condition, but the high speed digital synthesis of Bessel waveforms is far from trivial. In practice, lock-in amplifiers are commonly used with sine/cosine demodulation. For both the sine and the square wave case of the present invention, the condition is optimal between about 2.4 to 2.7 radians of PEM modulation amplitude.

While the present invention has been described in terms of preferred embodiments, it will be appreciated by one of ordinary skill in the art that modifications may be made without departing from the teachings and spirit of the foregoing. Moreover, it will be understood that the systems for imaging polarization properties described above, while often considering linear birefringence or retardance or Stokes parameters, can be readily adapted for many other properties, such as circular dichroism (also known as circular extinction), and circular birefringence (also known as circular retardance).

The invention claimed is:

1. A method of triggering a light source in an optical train that is configured so that the source light emanating from the source passes through a sample and through a first photoelastic modulator (PEM) that is operable with a first modulation frequency, through a second PEM that is operable with a second modulation frequency, and to an imaging device having an operation frequency, comprising:
    providing a light source that can be triggered between an ON and OFF state;
    generating a first pulse train corresponding to the first modulation frequency;
    generating a second pulse train corresponding to the second modulation frequency;
    generating triggering pulses during instances when the first and second pulse trains are in synchrony; and
    triggering the light source to be in the ON state only in response to the triggering pulses.

2. The method of claim 1, further comprising varying the wavelengths of the source light.

3. The method of claim 1, further comprising operating the imaging device as an intensity integrator.

4. The method of claim 1, wherein the imaging device operation frequency is at least an order of magnitude slower than the first or second modulation frequencies.

5. The method of claim 1, wherein the first and second modulation frequencies are not equal to one another.

6. A method of triggering a light source in an optical train that is configured so that the source light emanating from the source passes through a sample and through a first PEM that is operable with a first modulation frequency, through a second PEM that is operable with a second modulation frequency, and to an imaging device that provides image data corresponding to the light incident thereon, comprising:
    providing a light source that can be triggered between an ON and OFF state;
    sequentially operating the first and second PEMs such that only one PEM is operated at any time;
    generating first and second triggering pulses respectively corresponding to the first and second modulation frequencies; and
    sequentially triggering the light source with the first and second triggering pulses.

7. The method of claim 6, including sequentially collecting image data in relation to the sequential operation of the PEMs.

8. The method of claim 6, further comprising varying the wavelengths of the source light.

9. The method of claim 6, wherein generating the first triggering pulse comprises generating the first triggering pulse at each of four discrete phases of the first PEM operation cycle.

10. A method of triggering a light source in an optical train that is configured so that the source light emanating from the source passes through a sample and through a PEM that is operable with a modulation frequency to an imaging device that provides image data corresponding to the light incident thereon, comprising:
    providing a light source that can be triggered between an ON and OFF state;
    generating triggering pulses corresponding to the PEM modulation frequency; and
    triggering the light source with the triggering pulses.

11. The method of claim 10, including varying the wavelength of the source light.

* * * * *